(12) United States Patent
Zeis

(10) Patent No.: US 7,968,097 B2
(45) Date of Patent: Jun. 28, 2011

(54) IDENTIFICATION OF HLA-A2-PRESENTED T-CELL EPITOPES DERIVED FROM THE ONCOFOETAL ANTIGEN-IMMATURE LAMININ RECEPTOR PROTEIN AND USES THEREOF

(75) Inventor: Matthias Zeis, Hamburg (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 497 days.

(21) Appl. No.: 11/912,668

(22) PCT Filed: Apr. 26, 2006

(86) PCT No.: PCT/EP2006/003888
§ 371 (c)(1),
(2), (4) Date: Jan. 18, 2008

(87) PCT Pub. No.: WO2006/114307
PCT Pub. Date: Nov. 2, 2006

(65) Prior Publication Data
US 2009/0041794 A1    Feb. 12, 2009

(30) Foreign Application Priority Data
Apr. 26, 2005  (EP) .................................. 05009095

(51) Int. Cl.
*A61K 38/00* (2006.01)
*A61K 38/04* (2006.01)
*A61K 39/00* (2006.01)
*C07K 7/00* (2006.01)
*C07K 17/00* (2006.01)

(52) U.S. Cl. ...................... 424/185.1; 530/328; 530/327; 530/326; 530/325; 530/350; 536/23.5; 435/320.1; 435/69.1; 435/372.3

(58) Field of Classification Search ........................ None
See application file for complete search history.

(56) References Cited

FOREIGN PATENT DOCUMENTS
WO          02078524       10/2002
WO         2004012681       2/2004
WO    WO 2004012681 A2 *  2/2004

OTHER PUBLICATIONS

Siegel et al., (Blood. Dec. 15, 2003;102(13):4416-23. Epub Jul. 17, 2003).*
Database Uniprot [Online] Nov. 1996, "Potential Laminin-Binding Protein (Fragment)." XP002344539 Retrieved From EBI Accession No. Uniprot: Q29231_PIG Database Accession No. Q29231 Amino Acid Sequence.

(Continued)

Primary Examiner — Cherie M Woodward
(74) Attorney, Agent, or Firm — Baker Donelson Bearman, Caldwell & Berkowitz, PC

(57) ABSTRACT

The present invention relates to the immunotherapB of cancer, in particular several tumor entities including hematological malignancies. The present invention relates to tumor-associated T-helper cell peptide epitopes, alone or in combination with other tumor-associated peptides, that serve as active pharmaceutical ingredients of vaccine compositions that stimulate anti-tumor immune responses. In particular, the present invention relates to two novel peptide sequences derived from HLA class I or II molecules of human oncofoetal antigen immature laminin receptor (OFA/iLR), which can be used in vaccine compositions for eliciting anti-tumor immune responses.

8 Claims, 10 Drawing Sheets

OTHER PUBLICATIONS

A. K. Wintero et al: "Evaluation and Characterization of a Porcine Small Instestine CDNA Library: Analysis of 839 Clones." Mammalian Genome: Official Journal of the International Mammalian Genome Society. Jul. 1996, vol. 7, No. 7, Jul. 1996, pp. 509-517 ISSN: 0938-8990.

Database Uniprot [Online] Aug. 1992, "40S Ribosomal Protein SA (P40) (C10 Protein)." XP002364021 Retrieved From EBI Accession No. Uniprot: RSSA_Bovin Database Accession No. P26452 Sequence.

Database Uniprot [Online] Oct. 1, 1996, "40S Ribosomal Protein SA (P40) (34/67 KDA Laminin Receptor) (37LRP)." XP002364022 Retrieved From EBI Accession No. Uniprot: RSSA_Chick Database Accession No. P508950 Sequence.

International Search Report for PCT/EP2006/003888 Dated Sep. 7, 2006.

Sandra Siegel et al. "Identification of HLA-A 0201-Presented T Cell Epitopes Derived From the Oncofetal Antigen-Immature Laminin Receptor Protein in Patients With Hematological Malignancies" Journal of Immunology, 2006, 176: 6935-6944.

Database Geneseq [Online] Jan. 29, 2003, "Human Expressed Protein TAG (EPT) #1444." XP002387968 Retrieved From EBI Accession No. GSN: ABU04778. Database Accession No. ABU04778.

Database Geneseq [Online] Jan. 29, 2003, "Human Expressed Protein TAG (EPT) #1335." XP002387969, Retrieved From EBI Accession No. GSP: ABU04669; Database Accession No. ABU04669.

* cited by examiner (A)

(B)

(A)

(B)

(A)

(B)

(A)

(B)

IDENTIFICATION OF HLA-A2-PRESENTED T-CELL EPITOPES DERIVED FROM THE ONCOFOETAL ANTIGEN-IMMATURE LAMININ RECEPTOR PROTEIN AND USES THEREOF

RELATED APPLICATIONS

This application is the National Stage of PCT/EP2006/003888, filed Apr. 26, 2006, which claims priority to European Patent Application No. 05009095.0, filed Apr. 26, 2005, the entire contents of which are hereby incorporated.

The present invention relates to immunotherapeutic methods, and molecules and cells for use in immunotherapeutic methods. In particular, the present invention relates to the immunotherapy of cancer, in particular several tumor entities including hematological malignancies. The present invention furthermore relates to tumor-associated T-helper cell peptide epitopes, alone or in combination with other tumor-associated peptides, that serve as active pharmaceutical ingredients of vaccine compositions that stimulate anti-tumor immune responses. In particular, the present invention relates to two novel peptide sequences derived from HLA class I or II molecules of human oncofoetal antigen immature laminin receptor (OFA/ILR), which can be used in vaccine or other pharmaceutical compositions for eliciting anti-tumor immune responses.

For the purposes of the present invention, all references as cited herein are incorporated by reference in their entireties.

BACKGROUND OF THE INVENTION

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., Annals N.Y. Acad. Sci. 1993 690:101-112; Rosenberg S A. Shedding light on immunotherapy for cancer. N Engl J. Med. 2004 Apr. 1; 350(14):1461-3.). CD8+ T-cells (TCD8+) in particular, which recognize Class I molecules of the major histocompatibility complex (MHC)-bearing peptides of usually 8 to 10 residues derived from proteins located in the nucleus or the cytosol, or from defective ribosomal proteins (DRIPs), play an important role in this response. DRIPs are an essential source-for peptides and constitute products of incomplete translation at the ribosomes and have-first been described by the group of J. Yewdell (Schubert U, Anton L C, Gibbs J, Norbury C C, Yewdell J W, Bennink J R. Rapid degradation of a large fraction of newly synthesized proteins by proteasomes. Nature. 2000 Apr. 13; 404(6779):770-4). The MHC molecules of the human are also designated as human leukocyte-antigens (HLA).

There are two major classes of MHC-molecules that can be recognized by T-cells bearing T cell receptors. MHC-1-molecules that can be found on most cells having a nucleus that present peptides that result from proteolytic cleavage of endogenous proteins and larger peptides. MHC-II-molecules can be found on professional antigen presenting cells (APC), such as Macrophages, Dendritic Cells, on B cells, on endothelial cells and on altered cells of tumors and tumor stroma which, under normal circumstances, do not express MHC class II-molecules on their cell surfaces, and present either peptides stemming exogenous proteins that are taken up by APCs during the course of endocytosis, or that otherwise enter the MHC class II compartment (MIIC) and are subsequently processed and loaded onto MHC class II complexes. Complexes of peptide and MHC-I are recognized by CD8+-positive cytotoxic T-lymphocytes, whereas complexes of peptide and MHC-II are recognized by CD4+-helper-T-cells (generally described in Immunobiology by Charles A., Jr. Janeway, Paul Travers, Mark Walport, Mark J. Shlomchik).

For a peptide to trigger (elicit) a cellular immune response, it must bind to an MHC-molecule. This process is dependent on the allele of the MHC-molecule and specific polymorphisms of the amino acid sequence of the peptide. MHC-class-1-binding peptides are usually 8-10 residues in length and contain two conserved residues ("anchor") in their sequence which interact with the corresponding binding groove of the MHC-molecule (see 2nd listing as published in Immunogenetics (Rammensee H, Bachmann J, Emmerich N P, Bachor O A, Stevanovic S. SYFPEITHI: database for MHC ligands and peptide motifs. Immunogenetics. 1999 November; 50(3-4): 213-9).

There are now numerous examples of both mouse and human TCD8+ that specifically recognize tumor cells and have therapeutic activity after adoptive transfer, in some cases inducing complete remission. However, despite the potential for T cells to eradicate tumors, it is obvious from the progressive growth of most cancers that many tumors escape recognition by TCD8+ in vivo. Though a variety of tumors have been found to be immunogenic, stimulation of an effective anti-tumor immune response has been difficult to demonstrate. Latest evidence shows that immunizations can lead to strong T cell responses against tumorassociated peptides (Speiser D E, Lienard D, Rufer N, Rubio-Godoy V, Rimoldi D, Lejeune F, Krieg A M, Cerottini J C, Romero P. Rapid and strong human CD8+ T-cell responses to vaccination with peptide, IFA, and CpG oligodeoxynucleot 7909. J Clin Invest. 2005 March; 115(3):739-46. Schag K, Schmidt S M, Muller M R, Weinschenk T, Appel S, Weck M M, Grunebach F, Stevanovic S, Rammensee H G, Brossart P. Identification of C-met oncogene as a broadly expressed tumor-associated antigen recognized by cytotoxic T-lymphocytes. Clin Cancer Res. 2004 Jun. 1; 10(11):3658-66.

Antigens that are recognized by the tumor specific cytotoxic T-lymphocytes, that is, their epitopes, can be molecules derived from all protein classes, such as enzymes, receptors, transcription factors, etc. A comprehensive listing of peptides binding to or eluted from MHC class I or class II molecules can be found on www.syfpeithi.org. Furthermore, tumor associated antigens, for example, can also be present in tumor cells only, for example as products of mutated genes, e.g. MHC class I ligands, which function as T cell epitopes, from K-ras, BCR-abl and mutated p53. Another important class of tumor associated antigens are tissue-specific structures, such as CT ("cancer testis")-antigens that are expressed in different kinds of tumors and in healthy tissue of the testis. Other tumor associated peptides binding to MHC molecules stem from genes, which are expressed in higher copy numbers in cancer cells compared to healthy cells of the same organ or tissue, as well as compared to healthy cells from other tissues, e.g. c-met (See Schag K, Schmidt S M, Muller M R, Weinschenk T, Appel S, Weck M M, Grunebach F, Stevanovic S, Rammensee H G, Brossart P. Identification of Cmet oncogene as a broadly expressed tumor-associated antigen recognized by cytotoxic Tlymphocytes. Clin Cancer Res. 2004 Jun. 1; 10(11):3658-66). Other tumor-associated peptides stem from antigens that are retained in tumor cells and not secreted (e.g., proteins from the mucin gene family). Other sources can be aberrant transcripts (frameshift) or peptides from junction sites of post-translational protein-protein fusions. A comprehensive listing of tumor associated antigens described in the scientific literature can be found on www.cancerimmunity.org.

Various tumor associated antigens have been identified. Further, much research effort is being expended to identify additional tumor associated antigens. Some groups of tumor associated antigens, also referred to in the art as tumor specific antigens, are tissue specific. Examples include, but are not limited to, tyrosinase for melanoma, PSA and PSMA for prostate cancer and chromosomal cross-overs such as bcr/abl in lymphoma. However, many tumor associated antigens that have been identified occur in multiple tumor types, and some, such as oncogenic proteins and/or tumor suppressor genes (tumor suppressor genes are, for example reviewed for renal cancer in Linehan W M, Walther M M, Zbar B. The genetic basis of-cancer of the kidney. J Urol. 2003 December; 170(6 Pt 1):2163-72), which-actually cause the transformation event, occur in nearly all tumor types. A more general review of genetic causes of human cancer can be found in The Genetic Basis of Human Cancer by Bert Vogelstein, Kenneth W. Kinzler, 2002). For example, normal cellular proteins that control cell growth and differentiation, such as p53 (which is an example for a tumor suppressor gene), ras, c-met, myc, pRB, VHL, and HER-2/neu, can accumulate mutations resulting in upregulation of expression of these gene products thereby making them oncogenic (McCartey et al. Cancer Research 1998 15:58 2601-5; Disis et al. Ciba Found. Symp. 1994 187:198-211). These mutant proteins can be the target of a tumor specific immune response in multiple types of cancer.

The oncofoetal antigen-immature laminin receptor protein (OFA/iLRP) is widely expressed in many types of human tumors including hematopoietic malignancies (Rohrer J W, Barsoum A L, Coggin J H Jr. The development of a new universal tumor rejection antigen expressed on human and rodent cancers for vaccination, prevention of cancer, and anti-tumor therapy. Mod Asp Immunobiol. 2001; 5: 191-195. Barsoum A L, Rohrer J W, Coggin J H. 37 kDa oncofoetal antigen is an autoimmunogenic homologue of the 37 kDa laminin receptor precursor. Cell Mol Biol Lett. 2000; 19: 5535-5542. Castronovo V. Laminin receptors and laminin-binding proteins during tumor invasion and metastasis. Invasion Metas. 1993; 13: 1-30. Coggin J H Jr, Barsoum, A L, Rohrer J W. Tumors express both unique TSTA and crossprotective 44 kDa oncofetal antigen. Immunol Today. 1998; 19, 405-408. Coggin J H Jr, Barsoum A L, Rohrer J W. 37 kilo Dalton oncofetal antigen protein and immature laminin receptor protein are identical, universal T-cell inducing immunogens on primary rodent and human cancers. Anticancer Res. 1999; 19, 5535-5542)[1] but is not present in normal adult differentiated tissues. OFA-iLRP can be specifically recognized by both T and B lymphocytes, making it an attractive target molecule for vaccination approaches in several cancer entities. Utilizing dendritic cells (DC) transfected with OFA-iLR-coding RNA, tumor-specific T cell responses against hematopoietic target cells could be generated both in vitro and in vivo (Siegel S, Wagner A, Kabelitz D et al. Coggin, J. Jr., Barsoum, A., Rohrer, J., Schmitz, N., Zeis, M. Induction of cytotoxic T cell responses against the oncofoetal antigenimmature laminin receptor for the treatment of hematological malignancies. Blood 2003; 102, 4416-4423.

U.S. Pat. No. 6,753,314 describes a purified protein complex comprising a first polypeptide and a second polypeptide, wherein said complex comprises the amino acid sequences of a first polypeptide (SMI1, SEQ ID NO: 359), and a second polypeptide (BAST, SEQ ID NO: 518), denoted as ProPair 267a-267b.

U.S. Pat. No. 4,861,710 discloses a clone comprising a recombinant cDNA clone for encoding cell surface receptor for laminin as well as respective probes.

For the proteins to be recognized by the cytotoxic T-lymphocytes as tumor-specific antigen, and to be useful in a therapy, particular prerequisites must be fulfilled. The antigen should be expressed mainly by tumor cells and not by normal healthy tissues or in rather small amounts. It is furthermore desirable; that the respective antigen is not only present in one type of tumor, but also present high concentrations (e.g. copy numbers per cell). The presence of epitopes in the amino acid sequence of the antigen is essential, since such peptide ("immunogenic peptide") that is derived from a tumor associated antigen should lead to an in vitro or in vivo T-cell-response.

Until now, numerous strategies to target antigens into the class II processing pathway have been described. It is possible to incubate antigen presenting cells (APCs) with the antigen of interest in order to be taken up and processed (Chaux, P., Vantomme, V., Stroobant, V., Thielemans, K., Corthals, J., Luiten, R., Eggermont, A. M., Boon, T. & van der, B. P. (1999) *J. Exp. Med.* 189, 767-778). Other strategies use fusion proteins that contain lysosomal target sequences. Expressed in APCs, such fusion proteins direct the antigens into the class II processing compartment (Marks, M. S., Roche, P. A., van Donselaar, E., Woodruff, L., Peters, P. J. & Bonifacino, J. S. (1995) J. Cell Biol. 131, 351-369, Rodriguez, F., Harkins, S., Redwine, J. M., de Pereda, J. M. & Whitton, J. L. (2001) J. Virol. 75, 10421-10430). Also, special liposomal formulations for the delivery of peptides and other active pharmaceutical ingredients to pAPC have been developed ((Walter S, Herrgen L, Schoor O, Jung G, Wernet D, Buhring H J, Rammensee H G, Stevanovic S. Cutting edge: predetermined avidity of human CD8 T cells expanded on calibrated MHC/anti-CD28-coated microspheres. J Immunol. 2003 Nov. 15; 171(10):4974-84. Another method involves external loading of MHC molecules of pAPC in vitro or in vivo. In this setting, APCs are incubated with an excess of peptides in cell culture media, leading to competition for binding to MHC molecules on the surface of the APC.

T-helper cells play an important role in orchestrating the effector function of CTLs in anti-tumor immunity. T-helper cell epitopes that trigger a T-helper cell response of the Th1 type support effector functions of CD8+ Killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

The major task in the development of a tumor vaccine is therefore the identification and characterization of novel tumor associated antigens and immunogenic T-helper epitopes derived therefrom, which can be recognized by CD4+ CTLs. It is therefore an object of the present invention, to provide novel amino acid sequences for such peptides that have the ability to bind to a molecule of the human major histocompatibility complex (MHC) class-I and trigger T cell responses against cells bearing the peptides in conjunction with MHC molecules on their cell surfaces.

SUMMARY OF THE INVENTION

In summary, the inventors identified for the first time two distinct HLA-A*0201-specific peptide epitopes derived from the OFA/iLR protein. These peptides represent useful tools for both conducting tumor immunological studies and vaccination strategies in OFA/iLRPexpressing malignancies.

The invention in a further aspect relates to a method of killing target cells in a patient which target cells express a polypeptide comprising an amino acid sequence as given herein, the method comprising administering to the patient an effective amount of a peptide according to the present invention or a nucleic acid according to the present invention or an expression vector according to the present invention, wherein the amount of said peptide or amount of said nucleic acid or amount of said expression vector is effective to provoke an anti-target cell immune response in said patient.

The invention in a further aspect relates to a method of killing target cells in a patient which target cells express a polypeptide comprising an amino acid sequence given according to the present invention, the method comprising administering to the patient an effective number of cytotoxic T lymphocytes (CTL) as defined according to the present invention.

The invention in a further aspect relates to a method of killing target cells in a patient which target cells express a polypeptide comprising an amino acid sequence as given according to the present invention, the method comprising the steps of (1) obtaining cytotoxic T lymphocytes (CTL) from the patient; (2) introducing into said cells a nucleic acid encoding a T cell receptor (TCR), or a functionally equivalent molecule, as defined according to the present invention; and (3) introducing the cells produced in step (2) into the patient.

Preferably, the target cells are cancer cells. More preferably, said cancer is leukemia or lymphoma which expresses the polypeptide which comprises an amino acid sequence as given according to the present invention.

DETAILED DESCRIPTION OF THE INVENTION

Figure 1:
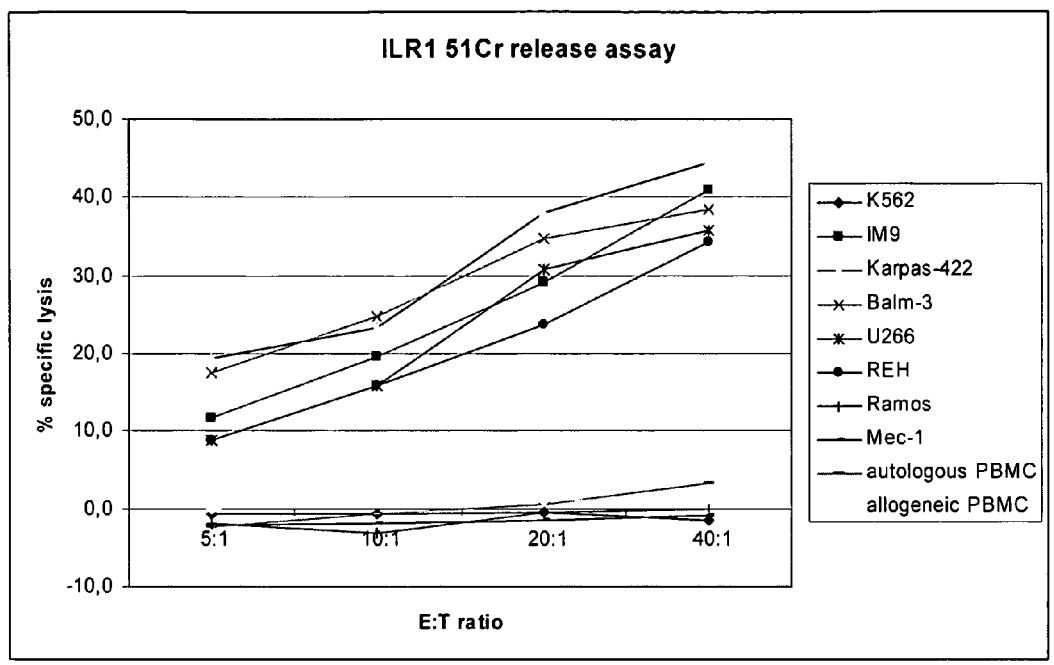
FIG. 1 shows the recognition of various cell lines by CTL specific for ILR1.

According to the present invention, this object is solved by providing a tumor associated peptide that is selected from the group of peptides comprising at least on sequence according to any of SEQ ID NO: 1 and SEQ ID NO: 2 of the attached sequence listing, wherein the peptide has the ability to bind to a molecule of the human major histocompatibility complex (MHC) class-I, comprising but not limited to the HLA allele expressed most frequently in Caucasian populations, HLA-A2 (including subtypes of HLAA2, such as HLA-A*0201).

The present invention further relates to two novel peptide sequences derived from HLA class I molecules of oncofoetal antigen-immature laminin receptor protein, which can be used in vaccine compositions for eliciting anti-tumor immune responses. The novel peptide sequences have been identified by a new and generally applicable combined approach for the identification of unknown naturally processed HLA class I ligands of defined—e.g. tumor associated—antigens. Thus, the inventors identified two distinct HLA-A*0201-specific T cell epitopes derived from the OFA/iLR-protein able to induce specific T cell reactivity against human tumor cells, including but not limited to various hematological malignancies.

A first aspect of the invention provides a peptide, comprising an amino acid sequence according to any of SEQ ID NO: 1 or SEQ ID NO: 2 or a variant thereof provided that the peptide is not the intact human polypeptide from which the amino acid sequence derived (i.e. oncofoetal antigen-immature laminin receptor protein (OFA/iLRP); for Accession number, see the attached table 1, below).

As described herein below, the peptides that form the basis of the present invention have both been identified as being presented by MHC class I bearing cells. Thus, these particular peptides as well as other peptides containing the sequence (i.e. derived peptides) will most likely both elicit a specific T-cell response, although the extent to which such response will be induced might vary from peptide to peptide. Differences, for example, could be caused due to mutations in said peptides (see below). The person of skill in the present art is well aware of methods that can be applied in order to determine the extent to which a response is induced by an individual peptide, in particular with reference to the examples herein and the respective literature.

Preferably, a peptide according to the present invention consists essentially of an amino acid sequence according to any of SEQ ID NO: 1 or SEQ ID NO: 2 or a variant thereof.

"Consisting essentially of" shall mean that a peptide according to the present invention, in addition to the sequence according to any of SEQ ID NO: 1 or SEQ ID NO: 2 or a variant thereof, contains additional N- and/or C-terminally located stretches of amino acids that do not necessarily form part of the peptide that functions as core sequence of the peptide comprising the binding motif and as an immunogenic T-helper epitope. Nevertheless, these stretches can be important to provide an efficient introduction of the peptide into cells.

By a "variant" of the given amino acid sequence, the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A, and so that it at least maintains, if not improves, the ability to generate activated CTL that can recognize and kill cells that express a polypeptide which contains an amino acid sequence as defined in the aspects of the invention. As can derived from the database as described in the following, certain positions of HLA-A binding peptides are typically anchor residues forming a core sequence fitting to the binding motif of the HLA binding groove.

Those amino acid residues that are not essential to interact with the T cell-receptor can be modified by replacement with another amino acid whose incorporation does not substantially effect T cell reactivity and does not eliminate binding to the relevant MHC. Thus, apart from the proviso given, the peptide of the invention may be any peptide (by which term the inventors include oligopeptide or polypeptide) that includes the amino acid sequences or a portion or variant thereof as given.

It is known that MHC-class II presented peptides are composed of a "core sequence" having a certain HLA-specific amino acid motif and, optionally, N- and/or C-terminal extensions that do not interfere with the function of the core sequence (i.e. are deemed as irrelevant for the interaction of the peptide and the T-cell). The N- and/or C-terminal extensions can be between 1 to 10 amino acids in length, respectively. Thus, a MHC-class II in vivo presented preferred peptide of the present invention exhibits an overall length of between 9 and 30 amino acids. These peptide can be used either directly to load MHC class II molecules or the sequence can be cloned into the vectors according to the description herein below. As these peptides form the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1000 residues, preferably fewer than 500 residues, more preferably fewer than 100 residues.

In another aspect of the present invention, similar to the situation as explained above for MHC class II molecules, the peptides of the present invention (although mainly related to MHC class I) may be used to trigger an MHC class II specific response, as ILR1 and ILR2 can exhibit simultaneous core- or partial sequences of HLA class II-molecules (matching with particular HLA class II-alleles as shown in the following tables). As above, the N- and/or C-terminal extensions can be between 1 to 10 amino acids in length, respectively. Thus, a preferred peptide of the present invention exhibits an overall length of between 9 and 30 amino acids. These peptide can be used either directly to load MHC class II molecules or the sequence can be cloned into the vectors according to the description herein below. As these peptides form the final product of the processing of larger peptides within the cell, longer peptides can be used as well. The peptides of this embodiment of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1000 residues.

TABLE A

ILR1-"Core sequences" having a certain HLA-specific amino acid motif for HLA class II-molecules. Matching amino acids are depicted in italic letters. Predictions were done by the computer programs PAProC (http://www.uni-tuebingen.de/uni/kxi/) and SYFPEITHY (http://www.syfpeithi.de).

HLA-DRB1*0101 15 - mers

| -3 | -2 | -1 | 1 | 2 | 3 | 4 | 5 | 6 | 7 | 8 | 9 | +1 | +2 | +3 | score |
|----|----|----|---|---|---|---|---|---|---|---|---|----|----|----|-------|
|    | T  | W  | E | K | L | L | A | A | R | A | I | V  | A  | I  | 26    |
|    |    |    |   |   |   |   |   |   |   |   |   |    |    |    |       |
|    | E  | K  | L | L | A | A | R | A | I | V | A | I  | E  | N  | 24    |

HLA-DRB1*0301 (DR17) 15 - mers

| -3 | -2 | -1 | 1 | 2 | 3 | 4 | 5 | 6 | 7 | 8 | 9 | +1 | +2 | +3 | score |
|----|----|----|---|---|---|---|---|---|---|---|---|----|----|----|-------|
| A  | R  | A  | I | V | A | I | E | N | P | A | D | V  | S  | V  | 19    |

HLA-DRB1*0401 (DR4Dw4) 15 - mers

| -3 | -2 | -1 | 1 | 2 | 3 | 4 | 5 | 6 | 7 | 8 | 9 | +1 | +2 | +3 | score |
|----|----|----|---|---|---|---|---|---|---|---|---|----|----|----|-------|
|    |    |    |   |   |   |   |   |   |   |   |   |    |    |    |       |
|    | E  | K  | L | L | A | A | R | A | I | V | A | I  | E  | N  | 20    |
|    |    |    |   |   |   |   |   |   |   |   |   |    |    |    |       |
|    | R  | A  | I | V | A | I | E | N | P | A | D | V  | S  | V  | 20    |

HLA-DRB1*0701 15 - mers

| -3 | -2 | -1 | 1 | 2 | 3 | 4 | 5 | 6 | 7 | 8 | 9 | +1 | +2 | +3 | score |
|----|----|----|---|---|---|---|---|---|---|---|---|----|----|----|-------|
|    | A  | R  | A | I | V | A | I | E | N | P | A | D  | V  | S  | V  20 |

HLA-DRB1*1501 (DR2b) 15 - mers

| -3 | -2 | -1 | 1 | 2 | 3 | 4 | 5 | 6 | 7 | 8 | 9 | +1 | +2 | +3 | score |
|----|----|----|---|---|---|---|---|---|---|---|---|----|----|----|-------|
|    | I  | N  | L | K | R | T | W | E | K | L | L | A  | A  | R  | 20    |
|    |    |    |   |   |   |   |   |   |   |   |   |    |    |    |       |
|    | R  | A  | I | V | A | I | E | N | P | A | D | V  | S  | V  | 18    |

TABLE B

ILR2-"Core sequences" having a certain HLA-specific amino acid motif for HLA class II-molecules. Matching amino acids are depicted in italic letters. Predictions were done by the computer programs PAProC (http://www.uni-tuebingen.de/uni/kxi/) and SYFPEITHY (http://www.syfpeithi.de).

HLA-DRB1*0101 15 - mers

| -3 | -2 | -1 | 1 | 2 | 3 | 4 | 5 | 6 | 7 | 8 | 9 | +1 | +2 | +3 | score |
|---|---|---|---|---|---|---|---|---|---|---|---|---|---|---|---|
| L | P | T | I | A | L | C | N | T | D | S | P | L | R | Y | 23 |

HLA-DRB1*0301 (DR17) 15 - mers

| -3 | -2 | -1 | 1 | 2 | 3 | 4 | 5 | 6 | 7 | 8 | 9 | +1 | +2 | +3 | score |
|---|---|---|---|---|---|---|---|---|---|---|---|---|---|---|---|

HLA-DRB1*0401 (DR4Dw4) 15 - mers

| -3 | -2 | -1 | 1 | 2 | 3 | 4 | 5 | 6 | 7 | 8 | 9 | +1 | +2 | +3 | score |
|---|---|---|---|---|---|---|---|---|---|---|---|---|---|---|---|
| Y | V | N | L | P | T | I | A | L | C | N | T | D | S | P | 20 |

HLA-DRB1*0701 15 - mers

| -3 | -2 | -1 | 1 | 2 | 3 | 4 | 5 | 6 | 7 | 8 | 9 | +1 | +2 | +3 | score |
|---|---|---|---|---|---|---|---|---|---|---|---|---|---|---|---|
| T | I | A | L | C | N | T | D | S | P | L | R | Y | V | D | 24 |

HLA-DRB1*11501 (DR2b) 15 - mers

| -3 | -2 | -1 | 1 | 2 | 3 | 4 | 5 | 6 | 7 | 8 | 9 | +1 | +2 | +3 | score |
|---|---|---|---|---|---|---|---|---|---|---|---|---|---|---|---|
| L | P | T | I | A | L | C | N | T | D | S | P | L | R | Y | 18 |

If a peptide of the present invention is greater than about 12 amino acid residues, and is used directly to bind to a MHC molecule, it is preferred that the residues that flank the core HLA binding region do not substantially affect the ability of the peptide to bind specifically to the binding groove of the MHC molecule or to present the peptide to the CTL. However, as already indicated above, it will be appreciated that larger peptides may be used, especially when encoded by a polynucleotide, since these larger peptides may be fragmented by suitable antigen-presentirlgceffs.

By "peptide" the inventors include not only molecules amino acid residues are joined by peptide (—CO—NH—) linkages but also molecules in which the peptide bond is reversed. Such retro-inverso peptidomimetics may be made using methods known in the art, for example such as those described in Meziere et al. (1997) J. Immunol. 159, 3230-3237, incorporated herein by reference. This approach involves making pseudopeptides containing changes involving the backbone, and not the orientation of side chains. Meziere et al. (1997) show that, at least for MHC class II and T helper cell responses, these pseudopeptides are useful. Retro-inverse peptides, which contain NH—CO bonds instead of CO—NH peptide bonds, are much more resistant to proteolysis.

Typically, the peptide of the invention is one which, if expressed in an antigen presenting cell, may be processed so that a fragment is produced that is able to bind to an appropriate MHC molecule and may be presented by a suitable cell and elicit a suitable T cell response. It will be appreciated that a fragment produced from the peptide may also be a peptide of the invention. Conveniently, the peptide of the invention contains a portion that includes the given amino acid sequence or a portion or variant thereof and a further portion which confers some desirable property. For example, the further portion may include a further T cell epitope (whether or not derived from the same polypeptide as the first T cell epitope containing portion) or it may include a carrier protein or peptide. Thus, in one embodiment the peptide of the invention is a truncated human protein or a fusion protein of a protein fragment and another polypeptide portion, provided that the human portion includes one or more inventive amino acid sequences.

In a particularly preferred embodiment, peptides of the invention includes the amino acid sequence of the invention and at least one further T cell epitope wherein the further T cell epitope is able to facilitate the production of a T cell response directed at the type of tumor that expresses a tumor-associated antigen. Thus, peptides of the invention include so-called "beads on a string" polypeptides which can also be used as vaccines.

It will be appreciated from the following that in some applications peptides of the invention may be used directly (i.e. they are not produced by expression of a polynucleotide in a patient's cell or in a cell given to a patient); in such applications it is preferred that the peptide has fewer than 100 or 50 residues. A preferred peptide of the present invention exhibits an overall length of between 9 and 30 amino acids.

Preferably the peptides of the invention are able to bind to HLA-A2, and more preferably bind selectively to HLA-A*0201.

By "aberrantly expressed" the inventors include the meaning that the polypeptide is overexpressed compared to normal levels of expression or that the gene is silent in the tissue from which the tumor is derived but in the tumor it is expressed. By "overexpressed" the inventors mean that the polypeptide is present at a level at least 1.2× that present in normal tissue; preferably at least 2× and more preferably at least 5× or 10× the level present in normal tissue.

Peptides (at least those containing peptide linkages between amino acid residues) may be synthesized by the Fmoc-polyamide mode of solid-phase peptide synthesis as disclosed by Lu et al. (1981) J. Org. Chem. 46,3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N dicyclohexyl-carbodiimide/lhydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized. Also a combination of solid phase and solution phase methodologies for the synthesis of peptides is possible (see, for example, Bruckdorfer T, Marder O, Albericio F. From production of peptides in milligram amounts for research to multi-tons quantities for drugs of the future. Curr Pharm Biotechnol. 2004 February; 5(1):29-43 and the-references as cited therein).

Trifluoroacetic acid is removed by evaporation in vacuo, with subsequent trituration with diethyl ether affording the crude peptide. Alternatively, a salt exchange can be used (TFA→acetic acid) before lyophilization. Any scavengers present are removed by a simple extraction procedure which on lyophilization of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography, hydrophobic interaction chromatography and (usually) reverse-phase high performance liquid chromatography using acetonitril/water gradient separation.

Analysis of peptides may be carried out using thin layer chromatography, reverse-phase high performance liquid chromatography, amino-acid analysis after acid hydrolysis, Edman-Sequencing and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide of the invention. The polynucleotide may be DNA, cDNA, PNA, CNA, RNA or combinations thereof and it may or may not contain introns so long as it codes for the peptide. Of course, it is only peptides which contain naturally occurring amino acid residues joined by naturally occurring peptide bonds which are encodable by a polynucleotide. A still further aspect of the invention provides an expression vector capable of expressing a polypeptide according to the invention.

A variety of methods have been developed to operable link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al, (1988) Science 239, 487-491. This method may be used for introducing the DNA into a suitable vector, for example by engineering in suitable restriction sites, or it may be used to modify the DNA in other useful ways as is known in the art. In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al.; U.S. Pat. No. 4,530,901 issued 23 Jul. 1985 to Weissman; U.S. Pat. No. 4,582,800 issued 15 Apr. 1986 to Crowl; U.S. Pat. No. 4,677,063 issued 30 Jun. 1987 to Mark et al.; U.S. Pat. No. 4,678,751 issued 7 Jul. 1987 to Goeddel; U.S. Pat. No. 4,704,362 issued 3 Nov. 1987 to Itakura et al.; U.S. Pat. No. 4,710,463 issued 1 Dec. 1987 to Murray, U.S. Pat. No. 4,757,006 issued 12 Jul. 1988 to Toole, Jr. et al.; U.S. Pat. No. 4,766,075 issued 23 Aug. 1988 to Goeddel et al.; and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells. Preferably, the system can be Awells cells.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells. An example of an inducible mammalian expression vector is pMSG, also available from Pharmacia. This vector uses the glucocorticoid-inducible promoter of the mouse mammary tumor virus long terminal repeat to drive expression of the cloned gene. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (Yips) and incorporate the yeast selectable markers HIS3, TRP1, LEU2 and URA3. Plasmids pRS413-416 are Yeast Centromere plasmids (Ycps). Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPHSO0 and YPHSO1 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells, which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al, (1972) Proc. Natl. Acad. Sci. USA 69, 2110 and Sambrook et al, (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) J. Mol. Biol. 98,503 or Berent et al. (1985) Biotech. 3,208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies. Thus, in addition to the transformed host cells themselves, the present invention also contemplates a culture of those cells, preferably a monoclonal (clonally homogeneous) culture, or a culture derived from a monoclonal culture, in a nutrient medium.

It will be appreciated that certain host cells of the invention are useful in the preparation of the peptides of the invention, for example bacterial, yeast and insect cells. However, other host cells may be useful in certain therapeutic methods. For example, antigenpresenting cells, such as dendritic cells, may usefully be used to express the peptides of the invention such that they may be loaded into appropriate MHC molecules.

A further aspect of the invention provides a method of producing a peptide for intravenous (i. v.) injection, subcutaneous (s. c.) injection, intradermal (i. d.) injection, intraperitoneal (i. p.) injection, intramuscular (i. m.) injection. Preferred methods of peptide injection are s.c., i.d., i.p., i.m., and i.v. Preferred methods of DNA injection are i.d., i.m., s.c., i.p. and i.v. Doses of between 1 and 500 mg of peptide or DNA may be given.

A further aspect of the invention provides a method of killing target cells in a patient, which target cells express a polypeptide comprising an amino acid sequence of the invention, the method comprising administering to the patient an effective amount of a peptide according to the invention, or an effective amount of a polynucleotide or an expression vector encoding the peptide, wherein the amount of the peptide or amount of the polynucleotide or expression vector is effective to provoke an anti-target cell immune response in the patient. The target cell is typically a tumor or cancer cell, in particular a leukemia or lymphoma cell.

The peptide or peptide-encoding nucleic acid may constitute a tumor or cancer vaccine. It may be administered directly into the patient, into the affected organ or systemically, or applied ex vivo to cells derived from the patient or a human cell line, which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant such as Detox, or used in combination with immune-stimulatory cytokines, or be administered with a suitable delivery system, for example liposomes. The peptide may also be conjugated to a suitable carrier such as keyhole limpet hemocyanin (KLH) or mannan (see WO 95/18145 and Longenecker et al. (1993) Ann. NY Acad. Sci. 690, 276-291). The peptide may also be tagged, or may be a fusion protein, or may be a hybrid molecule. Peptides of whose sequence is given in the present invention are expected to stimulate $CD8^+$ CTL. However, stimulation is more efficient in the presence of help provided by $CD4^+$ T cells. Thus, the fusion partner or sections of a hybrid molecule suitably provide epitopes that stimulate $CD4^+$ T cells. CD4+ stimulating epitopes are well known in the art and include those identified in tetanus toxoid. The polynucleotide may be substantially pure, or contained in a suitable vector or delivery system.

Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun" may also be used. The peptide or peptide encoded by the nucleic acid may be a fusion protein, for example with an epitope that stimulates $CD8^+$ T cells.

The peptide for use in a cancer vaccine may be any suitable peptide. In particular, it may be a suitable 9-mer peptide or a suitable 7-mer or 8-mer or 10-mer or 11-mer peptide or 12-mer. Longer peptides may also be suitable, but 9-mer or 10-mer peptides as described in the attached table 1 are preferred.

Suitably, any nucleic acid administered to the patient is sterile and pyrogen free. Naked DNA may be given intramuscularly or intradermally or subcutaneously. The peptides may be given intramuscularly, intradermally, intraperitoneally, intravenously or subcutaneously (see also above regarding the method of producing a peptide). Preferably, the peptides as active pharmaceutical components are given in combination with an adjuvant, such as, for example 11-2, IL-12, GM-CSF, incomplete Freund's adjuvant, complete Freund's adjuvant or liposomal formulations. Preferred adjuvants are described in, for example, Brinkman J A, Fausch S C, Weber J S, Kast W M. Peptide-based vaccines for cancer immunotherapy. Expert Opin Biol Ther. 2004 February; 4(2):181-98.

Vaccination results in CTL responses stimulated by professional antigen presenting cells; once CTL are primed, there may be an advantage in enhancing MHC expression in tumor cells.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al. (1995) Blood 86, 3295-3301; Roth et al, (1996) Scand. J. Immunology 43, 646-651). For example, targeting vectors may comprise a tissue- or tumor-specific promoter that directs expression of the antigen at a suitable place.

A further aspect of the invention therefore provides a vaccine effective against cancer, or cancer or tumour cells, comprising an effective amount of a peptide according to the invention, or comprising a nucleic acid encoding such a peptide. It is also preferred that the vaccine is a nucleic acid vaccine. It is known that inoculation with a nucleic acid vaccine, such as a DNA vaccine, encoding a polypeptide leads to a T cell response. Most preferred is a vaccine comprising a (synthetic) peptide or peptides (i.e. either alone or in combinations of 1, 2, 3, 4, 5 or 6 or even more peptides, see also further below).

Conveniently, the nucleic acid vaccine may comprise any suitable nucleic acid delivery means. The nucleic acid, preferably DNA, may be naked (i.e. with substantially no other components to be administered) or it may be delivered in a liposome or as part of a viral vector delivery system.

It is believed that uptake of the nucleic acid and expression of the encoded polypeptide by dendritic cells may occur through the mechanism of priming of the immune response; however, dendritic cells may not be transfected but are still important since they may pick up expressed peptide from transfected cells in the tissue.

Preferably vaccines of the present invention, such as DNA vaccine, are administered into the muscle or into the skin. The nucleic acid vaccine may be administered without adjuvant. The nucleic acid vaccine may also be administered with an adjuvant such as BCG or alum. Other suitable adjuvants include Aquila's QS21 stimulon (Aquila Biotech, Worcester, Mass., USA), which is derived from saponin, mycobacterial extracts and synthetic bacterial cell wall mimics, and proprietory adjuvants such as Ribi's Detox. Quil A, another saponin derived adjuvant, may also be used (Superfos, Denmark). Preferably the nucleic acid vaccine is administered without adjuvant. Other adjuvants such as Freund's may also be useful. It may also be useful to give the peptide conjugated to keyhole limpet hemocyanin, preferably also with an adjuvant.

Polynucleotide-mediated immunization therapy of cancer is described in Conry et al., (1996) Seminars in Oncology 23, 135-147; Condon et al., (1996) Nature Medicine 2, 1122-1127; Gong et al. (1997) Nature Medicine 3, 558-561; Zhai et al. (1996) J. Immunol. 156, 700-710; Graham et al. (1996) Int J. Cancer 65, 664-670; and Burchell et al. (1996) pp 309-313 In: Breast Cancer, Advances in biology and therapeutics, Calvo et al. (eds), John Libbey Eurotext, all of which are incorporated herein by reference.

A still further aspect of the present invention provides the use of a peptide according to the invention, or of a polynucleotide or expression vector encoding such a peptide, in the manufacture of a medicament for killing target cells in a patient, which target cells express a polypeptide comprising an amino acid sequence of the invention.

A further aspect of the invention provides a method for producing activated cytotoxic T lymphocytes (CTL) in vitro, the method comprising contacting in vitro CTL with antigen-loaded human class I MHC molecules expressed on the surface of a suitable antigenpresenting cell for a period of time sufficient to activate, in an antigen specific manner, said CTL wherein the antigen is a peptide according to the invention.

Suitably, the CTL are CD8+ helper cells. The MHC class I molecules may be expressed on the surface of any suitable cell and preferably the cell is one that does not naturally express MHC class I molecules (in which case the cell is transfected to express such a molecule) or, is defective in the antigen-processing or antigen-presenting pathways. In this way, it is possible for the cell expressing the MHC class I molecule to be primed substantially completely with a chosen peptide antigen before activating the CTL.

The antigen-presenting cell (or stimulator cell) typically has an MHC class I molecule on its surface and preferably is substantially incapable of itself loading said MHC class I molecule with the selected antigen. As is described in more detail below, the MHC class I molecule may readily be loaded with the selected antigen in vitro.

Preferably the mammalian cell lacks or has a reduced level or has reduced function of the TAP peptide transporter. TAP is the Transporter Associated with antigen Processing. Suitable cells which lack the TAP peptide transporter include T2, RMA-S and *Drosophila* cells.

The human peptide loading deficient cell-line T2 is available from the American Type Culture Collection, 12301 Parklawn Drive, Rockville, Md. 20852, USA under Catalogue No CRL 1992; incorporated herein by reference.

It is preferred that the host cell does not expresses substantially MHC class I molecules before transfection. It is also preferred that the stimulator cell expresses a molecule important for T cell co-stimulation, such as any of B7.1, B7.2, ICAM-1 and LFA 3.

The nucleic acid sequences of numerous MHC class I molecules, and of the co-stimulator molecules, are publicly available from the GenBank and EMBL databases.

In a further embodiment, combinations of HLA molecules may also be used, such as, for example, MHC-class II molecules as described in the Tables A and B herein. The use of recombinant polyepitope vaccines for the delivery of multiple $CD8^+$ CTL epitopes is described in Thomson et al. (1996) J. Immunol. 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, an amino acid sequence of the present invention and another $CD8^+$ T cell-stimulating epitope. Such a vaccine would be particularly useful for treating cancers. Such "bead-on-a-string" vaccines are typically DNA vaccines. The simultaneous triggering of an MHC class II-dependent immune response together with an MHC class I-dependent immune response has the advantage that this leads to a local $TH_1$ like T-cell-reaction of CD4-positive T-cells, whereby the MHC class I-dependent CD8-positive T-cells are supported.

A number of other methods may be used for generating CTL in vitro. For example, the methods described in Peoples et al, (1995) Proc. Natl. Acad. Sci. USA 92, 432-436 and Kawakami et al. (1992) J. Immunol. 148,638643 use autologous tumor-infiltrating lymphocytes in the generation of CTL. Plebanski et al. (1995) Eur. J. Immunol. 25, 1783-1787 makes use of autologous peripheral blood lymphocytes (PLBs) in the preparation of CTL. Jochmus et al. (1997) J. Gen. Virol. 78, 1689-1695 describes the production of autologous CTL by employing pulsing dendritic cells with peptide or polypeptide, or via infection with recombinant virus. Hill et al. (1995) J. Exp. Med. 181, 2221-2228 and Jerome et al. (1993) J. Immunol. 151, 1654-1662 make use of B cells in the production of autologous CTL. In addition, macrophages pulsed with peptide or polypeptide, or infected with recombinant virus, may be used in the preparation of autologous CTL. S. Walter et al, (Walter S, Herrgen L, Schoor O, Jung G, Wernet D, Buhring H J, Rammensee H G, Stevanovic S. Cutting edge: predetermined avidity of human CD8 T cells expanded on calibrated MHC/anti-CD28-coated microspheres. J Immunol. 2003 Nov. 15; 171(10):4974-8) describe the in vitro priming of T cells by using artificial antigen presenting cells, which is also a suitable way for generating T cells against the peptide of choice.

Allogeneic cells may also be used in the preparation of CTL and this method is described in detail in WO 97/26328, incorporated herein by reference. For example, in addition to *Drosophila* cells and T2 cells, other cells may be used to present antigens such as CHO cells, baculovirus-infected insects cells, bacteria, yeast, vaccinia-infected target cells. In addition plant viruses may be used (see, for example, Porta et al. (1994) Virology 202, 449-955, which describes the development of cowpea mosaic virus as a high-yielding system for the presentation of foreign peptides.

Activated CTL, which are directed against the peptides of the invention, are useful in therapy. Thus, a further aspect of the invention provides activated CTL obtainable by the foregoing methods of the invention.

A still further aspect of the invention provides activated CTL that selectively recognize a cell that expresses a polypeptide comprising an amino acid sequence of the invention. Preferably, the CTL recognizes the cell by interacting with the HLA/peptide-complex (for example, binding). The CTL are useful in a method of killing target cells in a patient, which target cells express a polypeptide comprising an amino acid sequence of the invention, wherein the patient is administered an effective number of the activated CTL. The CTL that are administered to the patient may be derived from the patient and activated as described above (i.e. they are autologous CTL). Alternatively, the CTL are not from the patient but are from another individual. Of course, a healthy individual is preferred. By "healthy individual" the inventors mean that the individual is generally in good health, preferably has a competent immune system and, more preferably, is not suffering from any disease which can be readily tested for, and detected.

The activated CTL express a T cell receptor (TCR) that is involved in recognizing cells that express the polypeptide. It is useful if the cDNA encoding the TCR is cloned from the activated CTL and transferred into a further CTL for expression.

In vivo, the target cells for the $CD8^+$ CTL according to the present invention can be cells of the tumor, leukemia or lymphoma (which express MHC class I) and/or stromal cells surrounding the tumor (tumor cells) (which sometimes also express MHC class I).

The TCRs of CTL clones of the invention specific for the peptides of the invention are cloned. The TCR usage in the CTL clones is determined using (i) TCR variable region-specific monoclonal antibodies and (ii) RT PCR with primers specific for Va and Vp gene families. A cDNA library is prepared from poly-A mRNA extracted from the CTL clones. Primers specific for the C-terminal portion of the TCR a and P chains and for the N-terminal portion of the identified Va and P segments are used. The complete cDNA for the TCR a and b chain is amplified with a high fidelity DNA polymerase and the amplified products cloned into a suitable cloning vector. The cloned a and P chain genes may be assembled into a single chain TCR by the method as described by Chung et al, (1994) Proc. Natl. Acad. Sci. USA 91, 12654-12658. In this single chain construct the VaJ segment is followed by the V DJ segment, followed by the Cp segment followed by the transmembrane and cytoplasmic segment of the CD3 chain. This single chain TCR is then inserted into a retroviral expression vector (a panel of vectors may be used based on their ability to infect mature human $CD8^+$ T lymphocytes and to mediate gene expression: the retroviral vector system Kat is one preferred possibility (see Finer et al. (1994) Blood 83, 43). High titer amphotrophic retrovirus are used to infect purified $CD8^+$ or $CD4^+$ T lymphocytes isolated from the peripheral blood of tumor patients (following a protocol published by Roberts et al. (1994) Blood 84, 2878-2889, incorporated herein by reference). Anti-CD3 antibodies are used to trigger proliferation of purified $CD8^+$ T cells, which facilitates retroviral integration and stable expression of single chain TCRs. The efficiency of retroviral transduction is determined by staining of infected CD8+ T cells with antibodies specific for the single chain TCR. In vitro analysis of transduced CD8+ T cells establishes that they display the same tumor-specific killing as seen with the allo-restricted CTL clone from which the TCR chains were originally cloned. Populations of transduced CD8+ T cells with the expected specificity may be used for adoptive immunotherapy of the tumor patients. Patients may be treated with in between $10^8$ to $10^{11}$ autologous, transduced CTL.

Other suitable systems for introducing genes into CTL are described in Moritz et al, (1994) Proc. Natl. Acad. Sci. USA 91, 4318-4322, incorporated herein by reference. Eshhar et al. (1993) Proc. Natl. Acad. Sci. USA 90, 720-724 and Hwu et al. (1993) J. Exp. Med. 178, 361-366 also describe the transfection of CTL. Thus, a further aspect of the invention provides a TCR that recognizes a cell that expresses a polypeptide comprising an amino acid sequence of the invention, the TCR being obtainable from the activated CTL.

In addition to the TCR, functionally equivalent molecules to the TCR are included in the invention. These include any molecule that is functionally equivalent to a TCR, which can perform the same function as a TCR. In particular, such molecules include genetically engineered three-domain single-chain TCRs as made by the method described by Chung et al. (1994) Proc. Natl. Acad. Sci. USA 91, 12654-12658, incorporated herein by reference, and referred to above. The invention also includes a polynucleotide encoding the TCR or functionally equivalent molecule, and an expression vector encoding the TCR or functionally equivalent molecule thereof. Expression vectors which are suitable for expressing the TCR of the invention include those described above in respect of expression of the peptides of the invention.

It is, however, preferred that the expression vectors are able to express the TCR in a CTL following transfection.

A still further aspect of the invention provides a method of killing target cells in a patient which target cells express a polypeptide comprising an amino acid sequence of the invention, the method comprising the steps of (1) obtaining CTL from the patient; (2) introducing into said cells a polynucleotide encoding a TCR, or a functionally equivalent molecule, as defined above; and (3) introducing the cells produced in step (2) into the patient.

A still further aspect of the invention provides a method of killing target cells in a patient, which target cells express a polypeptide comprising an amino acid sequence of the present invention and as discussed herein, the method comprising the steps of (1) obtaining antigen presenting cells, such as dendritic cells, from the patient; (2) contacting the antigen presenting cells with a peptide of the present invention as, or with a polynucleotide encoding such a peptide, ex vivo; and (3) reintroducing the so treated antigen presenting cells into the patient.

Preferably, the antigen presenting cells are dendritic cells. Suitably, the dendritic cells are autologous dendritic cells that are pulsed with an antigenic peptide. The antigenic peptide may be any suitable antigenic peptide that gives rise to an appropriate T cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278.

In a further embodiment, the antigen presenting cells, such as dendritic cells, are contacted with a polynucleotide that encodes a peptide of the invention. The polynucleotide may be any suitable polynucleotide and preferably capable of transducing the dendritic cell thus resulting in the presentation of a peptide and induction of immunity.

For convenience the polynucleotide may be comprised in a viral polynucleotide or virus. For example, adenovirus-transduced dendritic cells have been shown to induce antigen-specific anti-tumor immunity in relation to MUC1 (see Gong et al. (1997) Gene Ther. 4, 1023-1028). Similarly, adenovirus-based systems may be used (see, for example, Wan et al, (1997) Hum. Gene Ther. 8, 1355-1363); retroviral systems may be used (Specht et al. (1997) J. Exp. Med. 186, 1213-1221 and Szabolcs et al, (1997) Blood particle-mediated transfer to dendritic cells may also be used (Tuting et al. (1997) Eur. J. Immunol. 27, 2702-2707); and RNA may also be used (Ashley et al. (1997) J. Exp. Med. 186, 1177 1182).

It will be appreciated that, with respect to the methods of killing target cells in a patient, it is particularly preferred that the target cells are cancer cells, more preferably leukemia or lymphoma cancer cells.

It is particularly preferred that the patients who are treated by the methods of the invention have the HLA-A2 type. Thus, in a preferred embodiment the HLA haplotype of the patient is determined prior to treatment. HLA haplotyping may be carried out using any suitable method; such methods are well known in the art.

The invention includes the use of the peptides of invention (or polynucleotides encoding them) for active in vivo vaccination; for manipulation of autologous dendritic cells in vitro followed by introduction of the so-manipulated dendritic cells in vivo to activate CTL responses; to activate autologous CTL in vitro followed by adoptive therapy (i.e. the so-manipulated CTL are introduced into the patient); and to activate CTL from healthy donors (MHC matched or mismatched) in vitro followed by adoptive therapy.

In a preferred embodiment, vaccines of the present invention are administered to a host either alone or in combination with another cancer therapy to inhibit or suppress the formation of tumors.

The peptide vaccine may be administered without adjuvant. The peptide vaccine may also be administered with an adjuvant such as BCG or alum. Other suitable adjuvants include Aquila's QS21 stimulon (Aquila Biotech, Worcester, Mass., USA) which is derived from saponin, mycobacterial extracts and synthetic bacterial cell wall mimics, and proprietory adjuvants such as Ribi's Detox. QuilA, another saponin derived adjuvant, may also be used (Superfos, Denmark). Other adjuvants such as CpG oligonucleotides, stabilized RNA, Imiquimod (commercially available under the tradename Aldara™ from 3M Pharma, U.S.A.), Incomplete Freund's Adjuvant (commercially available as Montanide ISA-51 from Seppic S.A., Paris, France), liposomal formulations or GM-CSF may also be useful. It may also be useful to give the peptide conjugated to keyhole limpet hemocyanin, preferably also with an adjuvant.

The peptides according to the invention can also be used as diagnostic reagents. Using the peptides it can be analyzed, whether in a CTL-population CTLs are present that are specifically directed against a peptide or are induced by a therapy. Furthermore, the increase of precursor T-cells can be tested with those peptides that have a reactivity against the defined peptide. Furthermore, the peptide can be used as marker in order to monitor the progression of the disease of a tumor that expresses said antigen from which the peptide is derived.

In the attached Table 1, the peptides as used and identified are listed. In addition, in the table the respective position of the peptide in the respective protein is given. The Accession-Number of mouse-OFA/iLR in the Genbank of the "National Centre for Biotechnology Information" of the National Institute of Health (see http: www.ncbi.nlm.nih.gov) is AAD26866. The Accession-numbers of human-OFA/iLR in the Genbank of the "National Centre for Biotechnology Information" of the National Institute of Health (see http://www.ncbi.nlm.nih.gov) are, for example, AAC50652 or AAP35883.

In another preferred embodiment, peptides of the present invention are used for staining of leukocytes, in particular of T-lymphocytes. This use is of particular advantage if it should be proven, whether in a CTL-population specific CTLs are present that are directed against a peptide. Furthermore, the peptide can be used as marker for determining the progression of a therapy in a tumorous disease or disorder.

In another preferred embodiment of the present invention, the peptides are used for the production of an antibody. Polyclonal antibodies can be obtained in a standard fashion by immunization of animals via injection of the peptide and subsequent purification of the immune globulin. Monoclonal antibodies can be produced according to standard protocols such as described, for example, in Methods Enzymol. (1986), 121, Hybridoma technology and monoclonal antibodies.

The invention in a further aspect relates to a pharmaceutical composition, that contains one or more of said peptides according to the invention. This composition is used for parenteral administration, such as subcutaneous, intradermal, intramuscular or oral administration. Peptides of the present invention are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed., 2000, American Pharmaceutical Association and pharmaceutical press. The composition can be used for a prevention, prophylaxis and/or therapy of tumorous diseases.

The pharmaceutical preparation, containing at least one of the peptides of the present invention comprising any of the SEQ ID NO: 1 to SEQ ID NO: 2 is administered to a patient that suffers from a tumorous disease that is associated with the respective peptide or antigen. Particular diseases to be treated are malignancies expressing OFA/iLRP, such as leukemias (e.g. AML or CLL) or myelomas (e.g. MM). By this, a CTL-specific immune response can be triggered.

In another aspect of the present invention, a combination of two or several peptides according to the present invention can be used as vaccine, either in direct combination or within the same treatment regimen. Furthermore, combinations with other peptides, for example MHC class II specific peptides, can be used. The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analyzing the production of IFN-γ (see also examples below), IL-12 or Perforin. Usually, the most efficient peptides are then combined as a vaccine for the purposes as described above.

A suitable vaccine will contain 2, 3, 4, 5, 6, 7, 8, 9, 10, 11, 12, 13, 14 or 15 different peptides, preferably 4, 5, 6 or 7 different peptides, and most preferably 6 different peptides.

Finally, the vaccine can be dependent from the specific type of cancer to be treated is suffering from as well as the status of the disease, earlier treatment regimens, the immune status of the patient, and, of course, the HLA-haplotype of the patient.

Figure 11A:
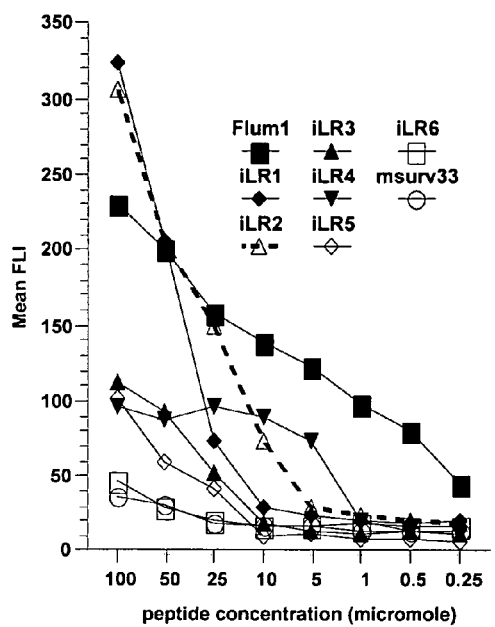
FIG. 11 shows the in vitro reconstitution assay using the TAP (transporter associated with antigen processing)-deficient T2 cell line, only two peptides (iLR1, iLR2) show strong binding affinity to HLA-A*0201 (FIGS. 11A and B), if compared with the Flu nucleoprotein58.66. Compared to ILR3 to ILR14 and the reference peptide from Influenza Virus (Flum 1), ILR1 and binding affinity for HLA-A*02.
Figure 11B:
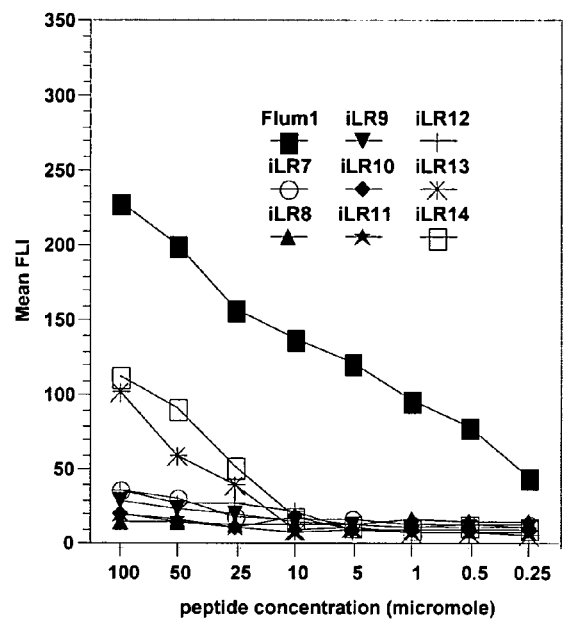

The identification of T-helper cell epitopes of tumor associated antigens remains an important task in anti-tumor immunotherapy. To identify T cell-binding epitopes deduced from the OFA-iLR protein, 14 peptides were synthesized (see below) that were predicted by the computer programs PAProC (http://www.uni-tuebingen.de/uni/kxi/) and SYFPEITHY (http://www.syfpeithi.de) to bind to the HLA-A*0201 molecule. In an in vitro reconstitution assay using the TAP (transporter associated with antigen processing)-deficient T2 cell line, only two peptides (iLR1, iLR2) showed strong binding affinity to HLA-A*0201 (FIGS. 11A and B) if compared with the Flu nucleoprotein58-66. In the presence of fully matured DC pulsed with either the iLR1 or iLR2 peptide CTL lines could be generated derived from healthy HLA-A*0201+ donors.

Peptide titration curves demonstrate that iLR1 and iLR2-specific CTL were of high affinity to the peptide/MHC complex (FIGS. 5 and 10). Both CTL lines specific for iLR1 (FIG. 1) or iLR2 (FIG. 6) elicited strong cytolytic activity against HLA-A*0201+ hematological tumor lines, primary malignant AML blasts (FIGS. 4A, B and 8A, B, respectively) and CLL cells (FIGS. 3A, B, and 9A, B, respectively) but spared HLA-A2-negative targets and normal hematopoietic cells (ibid). Antibody blocking experiments (FIGS. 2 and 7) revealed an MHC-class I-restricted killing induced by peptide specific CD8+ T lymphocytes. To determine the frequency of iLR1- and iLR2-specific T cells in HLAA*0201$^+$ AML, CLL and multiple myeloma patients, ELISPOT IFNl' secretion assay (Tables 3-5) were performed. In 25/50 (50%) and 20/50 (40%) of HLA-A*0201$^+$ patients with hematological malignancies significant levels of iLR1 or iLR2 peptide-specific T cells could be detected, whereas in peripheral blood samples of healthy individuals no spontaneous T cell responses against either ILR1 or ILR2 occurred (Table 2). In one patient with CLL and in another with AML, autologous CTL lines specific for both iLR1 and iLR2 peptide epitope could be generated eliciting efficient cytotoxic activity against autologous and allogeneic HLA-A2-matched target cells.

The inventors have previously shown that OFA/iLR-specific regulatory CD8$^+$ T cell clones secreting Interleukin-10 can be identified both in mice bearing an OFA/iLR$^+$ tumor (Rohrer J W, Rohrer S D, Barsoum A, Coggin J H Jr. Differential recognition of murine tumor-associated oncofoetal transplantation antigen and individually specific tumor transplantation antigens by syngeneic cloned Balb/c and RFM mouse T cells. J. Immunol. 1994; 152: 745-764) and in patients with advanced breast carcinomas (Rohrer J W, Barsoum A L, Dyess D L et al, Human breast carcinoma patients develop clonable oncofoetal antigen-specific effector and regulatory T lymphocytes. J. Immunol. 1999; 162: 6880-6892. 11. Rohrer J W, Coggin J H Jr. CD8 T cell clones inhibit antitumor T cell function by secreting IL-10. J. Immunol. 1995; 155: 5719.). Su et al. (Su Z et al, Immunological and Clinical responses in metastatic renal cancer patients vaccinated with tumor RNA-transfected dendritic cells. Cancer Res. 2003; 63: 2127-2133) reported T cells reactive against MHC class I-restricted epitopes from OFA/iLR from patients with metastatic renal cancer. In this study, the authors also report an unexpectedly low mortality of patients having received therapeutic vaccinations with autologous dendritic cells, which had been transfected with RNA encoding OFA/iLR and other putative tumor antigens. However, the number, HLA-restriction, and chemical identity of epitopes from OFA/iLR was not disclosed by Su et al. Further Höltl et al. (Höltl et al. Immunotherapy of metastatic renal cell carcinoma with tumor lysate-pulsed autologous dendritic cells. Clin. Cancer Res. 2002; 8: 3369-3376) delivered additional evidence that OFA/iLR may be very useful for cancer immunotherapy based on therapeutic vaccines stimulating specific cellular immune responses. The authors found that 5/6 patients with metastic renal cell carcinoma (RCC), who had been vaccinated with autologous dendritic cells loaded with autologous or allogeneic tumor cell lysates, featured enhanced immune responses against OFA/iLR. Again, no epitopes from OFA/iLR were disclosed by Höltl et al. Interestingly, the patients with the strongest immune responses against OFA/iLR had a complete and a partial clinical response.

In the inventors' small series of CLL patients with early disease (Binet A), no relevant IL-10-secreting T cells specific for the iLR1 or iLR2 peptide were detectable (data not shown). The inventors are currently involved with experiments to elucidate more precisely a possible relationship between the occurrence of anti-OFA/iLRP-specific T cells secreting IFN-γ or IL10 and the stage of disease in patients with CLL and multiple myeloma.

In summary, the inventors identified for the first time two distinct HLA-A*0201-specific peptide epitopes derived from the OFA/iLR protein. These peptides represent useful tools for both conducting tumor immunological studies and vaccination strategies in OFA/iLRPexpressing malignancies.

The invention in a further aspect relates to a method of killing target cells in a patient which target cells express a polypeptide comprising an amino acid sequence as given herein, the method comprising administering to the patient an effective amount of a peptide according to the present invention or a nucleic acid according to the present invention or an expression vector according to the present invention, wherein the amount of said peptide or amount of said nucleic acid or amount of said expression vector is effective to provoke an anti-target cell immune response in said patient.

The invention in a further aspect relates to a method of killing target cells in a patient which target cells express a polypeptide comprising an amino acid sequence given according to the present invention, the method comprising administering to the patient an effective number of cytotoxic T lymphocytes (CTL) as defined according to the present invention.

The invention in a further aspect relates to a method of killing target cells in a patient which target cells express a polypeptide comprising an amino acid sequence as given according to the present invention, the method comprising the steps of (1) obtaining cytotoxic T lymphocytes (CTL) from the patient; (2) introducing into said cells a nucleic acid encoding a T cell receptor (TCR), or a functionally equivalent molecule, as defined according to the present invention; and (3) introducing the cells produced in step (2) into the patient.

Preferably, the target cells are cancer cells. More preferably, said cancer is leukemia or lymphoma which expresses the polypeptide which comprises an amino acid sequence as given according to the present invention.

It should be understood that the features of the invention as disclosed and described herein can be used not only in the respective combination as indicated but also in a singular fashion without departing from the intended scope of the present invention.

The invention will now be described in more detail by reference to the following Figures, the Sequence listing, and the Examples. The following examples are provided for illustrative purposes only and are not intended to limit the invention.

EXAMPLES

Abbreviations used throughout the present application:
Ab: Antibody
Ag: Antigen
APC: antigen presenting cell
CD: Cluster of Differentiation
cpm: counts per minute
DC: Dendritic Cell
EBV: Epstein-Barr Virus
ESI: electrospray ionization
HLA: Human Leukocyte Antigen
HPLC: High Performance Liquid Chromatography
IFN: Interferon
Ii: invariant chain (CD74)
IL: Interleukin
MALDI: matrix assisted laser desorption/ionization
MHC: Major Histocompatibility Complex
MS: mass spectrometry
$OD_{450}$: Optical Density at a wavelength of 450 nm
PBMC: Peripheral Blood Mononuclear Cells
PCR: Polymerase Chain Reaction
PHA: Phytohemagglutinin
SDS-PAGE: Sodium Dodecyl Sulfate Polyacrylamide Gel Electrophoresis
S.I.: stimulation index
TOF: time of flight
Cell Lines, Tumor Samples and Peripheral Blood Mononuclear Cells (PBMC)

All cell lines used in this study were obtained from American Type Culture Collection (Manassas, Va., USA). PBMC, CD34+ progenitor cells, bone marrow cells and tumor samples were collected from healthy donors, patients with acute myeloidleukemia (AML), chronic lymphocytic leukemia (CLL) and multiple myeloma (MM), respectively, after informed consent and approval by the institutional review board.

Antibodies

Antibody against MAM-6: Alexis Corp., Switzerland, obtained through AXXORA DEUTSCHLAND GmbH, Gallusstrasse 10, D-35305 Grtinberg. Product-Nr. SIG-614. Antibody against HLA-A*02: clone BB7.2 from BD Pharmingen, Cat.-Nr. 551230. Antibody against CD8: clone SFC121Thy2D3 (T8) from Beckman Coulter, Part.-Nr. 6602139. Antibody against TCR: clone BMA031 from Beckman Coulter, Part-Nr. IM1466. Antibody against CD4: clone SFCI12T4D11 (T4) from Beckman Coulter, Part.-Nr. 6602138. Antibody against HMFG-1: clone 1.10.F3 from Beckman Coulter, Part.-Nr.IMO271.

Peptides

The peptides F1uM1$_{58-66}$ (GILGFVFTL) (SEQ ID NO:3), HIV-Pol$_{476-484}$ (ILKEPVHGV, negative control in ELISPOT assay) (SEQ ID NO:4), msurv33 (LYLKNYRIA, murine survivin peptide epitope specific for $H2^d$, negative control in T2 binding assays) (SEQ ID NO:5), iLR1$_{59-68}$ (LLAARAIVAI) (SEQ ID NO:1), iLR2$_{146-154}$ (ALCNTDSPL) (SEQ ID NO:2), iLR3$_{60-68}$ (LAARAIVAI) (SEQ ID NO:6), iLR4$_{58-66}$ (LLLAARAIV) (SEQ ID NO:7), iLR5$_{7-15}$ (VLQMKEEDV) (SEQ ID NO:8), iLR6$_{50-58}$ (NLKRTWEKL) (SEQ ID NO:9), iLR7$_{66-74}$ (VAIENPADV) (SEQ ID NO:10), iLR8$_{139-147}$ (YVNLPTIAL) (SEQ ID NO:11), iLR9$_{177-185}$ (MLAREVLRM) (SEQ ID NO:12), iLR10$_{249-257}$ (SEGVQVPSV) (SEQ ID NO:13), iLR11$_{18-26}$ (FLAAGTHLG) (SEQ ID NO:14), iLR12$_{57-66}$ (KLLLAARAIV) (SEQ ID NO:15), iLR13$_{67-76}$ (AIENPADVSV) (SEQ ID NO:16), iLR14$_{173-182}$ (LMWWMLAREV) (SEQ ID NO:17), were purchased from Biosynthan (Berlin, Germany) provided with more than 90% purity and were analyzed by high-performance liquid chromatography and mass spectrometry.

Peptide Synthesis and Analysis

Peptides were synthesized in an automated peptide synthesizer EPS221 (Abimed, Langenfeld, Germany) following the Fmoc/tBu strategy. After removal from the resin by treatment with TFA/phenol/ethanedithiol/thioanisole/water (90/3.75/1.25/2.5 by vol.) for 1 h or 3 h (arginine-containing peptides) peptides were precipitated from metIfyl-tert. butyl ether, washed once with methyl-tert. butyl ether and twice with diethyl ether and resuspended in water prior to lyophilization. Synthesis products were analyzed by HPLC (Varian star, Zinsser analytics, MUnchen, Germany) and MALDI-TOF mass spectrometry (future, GSG, Bruchsal, Germany). Peptides of less than 80% purity were purified by preparative HPLC.

T2-binding Assay

The T2 whole cell-binding assay was performed using a protocol adopted from Casati et al. The apoptosis inhibitor protein survivin induces tumor-specific $CD8^+$ and $CD4^+$ T cells in colorectal cancer patients. Cancer Res. 2003; 63, 4507-4515.).

Generation of Human CTL

CTL derived from healthy HLA-A*0201$^+$ individuals were generated using a protocol described elsewhere (Zeis M, Siegel S, Schmitz M et al. Induction of cytotoxic T lymphocytes against hematologic neoplasms by survivin RNA-transfected dendritic cells. J Immunol. 2003; 170, 5391-5397.). For the induction of autologous OFA/ILR, peptide-specific CTL obtained from patients with AML and CLL, $CD8^+$ T cells were separated from PBMC using immunomagnetic beads (MACS®, Miltenyi, Bergisch-Gladbach, Germany), cultured with autologous OFA/iLR peptide-pulsed fully matured DC and restimulated with autologous peptide-pulsed PBMC in the presence of IL-2 (1 ng/ml, CellConcepts, Weisskirch, Germany). After at least four weekly restimulations, CTL reactivity was determined in a conventional 4 h $^{51}$Chromium release assay. Cold target inhibition assays and antibody blocking experiments were performed as previously described (Zeis M, Siegel S, Schmitz M et al. Induction of cytotoxic T lymphocytes against hematologic neoplasms by survivin RNA-transfected dendritic cells. J Immunol. 2003; 170, 5391-5397.).

ELISPOT Assay

To determine the frequency of OFA/iLR peptide-specific T cells in patients, ELISPOT-assays were performed using the Interferon-γ-ELISPOT-Kit (Becton Dickinson, Heidelberg, Germany) according to manufacturer's instructions.

TABLE 1

Peptides and tumor-associated T-helper cell peptide epitopes as identified in the present invention

| Name | Sequence | SEQ ID-NO: | Note |
|---|---|---|---|
| 1. iLR1$_{59-68}$ | LLAARAIVAI | SEQ ID-NO:1 | ILR1 |
| 2. iLR2$_{146-154}$ | ALCNTDSPL | SEQ ID-NO:2 | ILR2 |
| 3. FluM1$_{58-66}$ | GILGFVFTL | SEQ ID-NO:3 | |
| 4. Hiv-Pol$_{476-484}$ | ILKEPVHGV | SEQ ID-NO:4 | negative control in ELISPOT assay |
| 5. msurv33 | LYLKNYRIA | SEQ ID-NO:5 | murine survivin peptide epitope specific for H2$^d$, negative control in T2 binding assays |
| 6. iLR3$_{60-68}$ | LAARAIVAI | SEQ ID-NO:6 | |
| 7. iLR4$_{58-66}$ | LLLAARAIV | SEQ ID-NO:7 | |
| 8. iLR5$_{7-15}$ | VLQMKEEDV | SEQ ID-NO:8 | |
| 9. iLR6$_{50-58}$ | NLKRTWEKL | SEQ ID-NO:9 | |
| 10. iLR7$_{66-74}$ | VAIENPADV | SEQ ID-NO:10 | |
| 11. iLR8$_{139-147}$ | YVNLPTIAL | SEQ ID-NO:11 | |
| 12. iLR9$_{177-185}$ | MLAREVLRM | SEQ ID-NO:12 | |
| 13. iLR10$_{249-257}$ | SEGVQVPSV | SEQ ID-NO:13 | |
| 14. iLR11$_{18-26}$ | FLAAGTHLG | SEQ ID-NO:14 | |

TABLE 1-continued

Peptides and tumor-associated T-helper cell peptide epitopes as identified in the present invention

| Name | Sequence | SEQ ID-NO: | Note |
|---|---|---|---|
| 15. iLR12$_{57-66}$ | KLLLAARAIV | SEQ ID-NO: 15 | |
| 16. iLR13$_{67-76}$ | AIENPADVSV | SEQ ID-NO: 16 | |
| 17. iLR14$_{173-182}$ | LMWWMLAREV | SEQ ID-NO: 17 | |

Results Peptides: ILR1 (LLAARAIVAI, SEQ ID NO: 1) and ILR2 (ALCNTDSPL, SEQ ID NO: 2)

In all ELISPOT analyses, the numbers given for IFN-gamma-positive spots are per 105 PBMC. Prior to analysis, T cells from patients and healthy donors had been kept in culture for seven days in the presence of Interleukin-2 (IL microgram/$10^6$ PBMC/milliliter).

All healthy donor samples probed have low numbers of CTL responding to ILR1 or ILR2 (Table 2) in IFN-γ ELISPOT analysis.

Of all CLL patient tumor samples probed, 12/20 (60%) have significant (>20) CTL responses against ILR1 peptide, and 9/16 (56%) have responses against ILR2 peptide in IFN-γ ELISPOT analysis. The median numbers of positively stained CTL for the two ILR-derived peptides compare to 55% (ILR2) and 76% (ILR1) of the numbers of responses obtained with a common HLA-A*02-restricted recall-antigen from Influenza Matrix protein, against which nearly every adult should have had cellular immune responses before (Table 3).

TABLE 2

| Indication: | healthy donors | | |
|---|---|---|---|
| Patients probed positive for: | HLA-A*02 | | |
| ELISPOT detecting: | Interferon gamma (IFN-γ) | | |
| Peptide amino acid sequence: | LLAARAIVAI SEQ ID NO:1 | ALCNTDSPL SEQ ID NO:2 | GILGFVFTL SEQ ID NO:3 |
| peptide designation: | ILR1 | ILR2 | FluM1 |
| Source protein: | Immature Laminin Receptor Protein | Immature Laminin Receptor Protein | Influenza Matrix Protein M1 |
| patient name: | # of positively stained spots: | | |
| 001 | 0 | 0 | |
| 002 | 3 | 3 | |
| 003 | 2 | 2 | |
| 004 | 4 | 4 | |
| 005 | 5 | 5 | |
| 006 | 4 | 4 | |
| 007 | 6 | 6 | |
| 008 | 7 | 7 | |
| 009 | 0 | 0 | |
| 010 | 0 | 0 | |
| 011 | 0 | 0 | |
| 012 | 0 | 0 | |
| 013 | 3 | 3 | |
| 014 | 4 | 4 | |
| 015 | 5 | 5 | |

TABLE 3

| | | | |
|---|---|---|---|
| Indication: | CLL patients | | |
| Patients probed positive for: | HLA-A*02 | | |
| ELISPOT detecting: | Interferon gamma (IFN-γ) | | |
| Peptide amino acid sequence: | LLAARAIVAI SEQ ID NO: 1 | ALCNTDSPL SEQ ID NO:2 | GILGFVFTL SEQ ID NO:3 |
| peptide designation: | ILR1 | ILR2 | FluM1 |
| Source protein: | Immature Laminin Receptor Protein | Immature Laminin Receptor Protein | Influenza Matrix Protein M1 |
| patient name: | # of positively stained spots: | | |
| 000, B. | 4 | 4 | 15 |
| 000, T. | 56 | 45 | 35 |
| 022, E. | 77 | 65 | 51 |
| 027, W. | 88 | 128 | 35 |
| 033, D. | 122 | 67 | n.d. |
| 038, N. | 45 | 23 | 140 |
| 041, E. | 35 | 27 | 65 |
| 049, G. | 56 | 78 | 31 |
| 052, G. | 0 | 56 | n.d. |
| 054, S. | 0 | 0 | 47 |
| 058, E. | 0 | 0 | 41 |
| 060, F. | 0 | 0 | 63 |
| 065, B. | 1 | 0 | 58 |
| 070, M. | 2 | 2 | 89 |
| 071, G. | 3 | 0 | 91 |
| 082, G. | 68 | | 28 |
| 083, M. | 100 | | 279 |
| 087, N. | 83 | | 24 |
| 090, G. | 121 | | 30 |
| 091, G. | 93 | | 67 |
| 125, F. | | 57 | |

Of all AML patient tumor samples probed, 6/15 (40%) have significant (>20) CTL responses 5 against ILR1 peptide, and 7/15 (47%) have responses against ILR2 peptide in IFN-γ ELISPOT analysis (Table 4).

TABLE 4

| Indication: | AML patients | | |
|---|---|---|---|
| Patients probed positive for: | HLA-A*02 | | |
| ELISPOT detecting: | Interferon gamma (IFN-γ) | | |
| Peptide amino acid sequence: | LLAARAIVAI SEQ ID NO: 1 | ALCNTDSPL SEQ ID NO:2 | GILGFVFTL SEQ ID NO:3 |
| peptide designation: | ILR1 | ILR2 | FluM1 |
| Source protein: | Immature Laminin Receptor Protein | Immature Laminin Receptor Protein | Influenza Matrix Protein M1 |
| patient name: | # of positively stained spots: | | |
| 000, M. | 2 | 0 | |
| 025, J. | 3 | 0 | |
| 041, G. | 2 | 0 | |
| 055, C. | 1 | 1 | |
| 072, G. | 3 | 3 | |
| 106, K. | 4 | 0 | |
| 107, L. | 5 | 3 | |
| 108, J. | 56 | 34 | |
| 110, B. | 54 | 27 | |
| 000, M. | 34 | 34 | |
| 026, C | 34 | 34 | |
| 043, L. | 33 | 23 | |
| 056, N. | 25 | 112 | |
| 072, G. | 1 | 1 | |
| 068, G. | 2 | 32 | |

Of all myeloma patient tumor samples probed, 8/14 (57%) have significant (>20) CTL responses against ILR1 peptide, and 6/14 (43%) have responses against ILR2 peptide in IFN-γ ELISPOT analysis (Table 5).

TABLE 5

| Indication: | Myeloma | | |
|---|---|---|---|
| Patients probed positive for: | HLA-A*02 | | |
| ELISPOT detecting: | Interferon gamma (IFN-γ) | | |
| Peptide amino acid sequence: | LLAARAIVAI SEQ ID NO: 1 | ALCNTDSPL SEQ ID NO:2 | GILGFVFTL SEQ ID NO:3 |
| peptide designation: | ILR1 | ILR2 | FluM1 |
| Source protein: | Immature Laminin Receptor Protein | Immature Laminin Receptor Protein | Influenza Matrix Protein M1 |
| patient name: | # of positively stained spots: | | |
| 001 | 3 | 0 | |
| 002 | 4 | 0 | |
| 003 | 56 | 0 | |
| 004 | 76 | 1 | |

TABLE 5-continued

| 005 | 56 | 3 |
|---|---|---|
| 006 | 43 | 0 |
| 007 | 22 | 3 |
| 008 | 23 | 34 |
| 009 | 0 | 27 |
| 010 | 0 | 34 |
| 011 |  | 34 |
| 012 | 23 | 23 |
| 013 | 112 | 112 |
| 014 | 1 | 1 |

Figure 12:
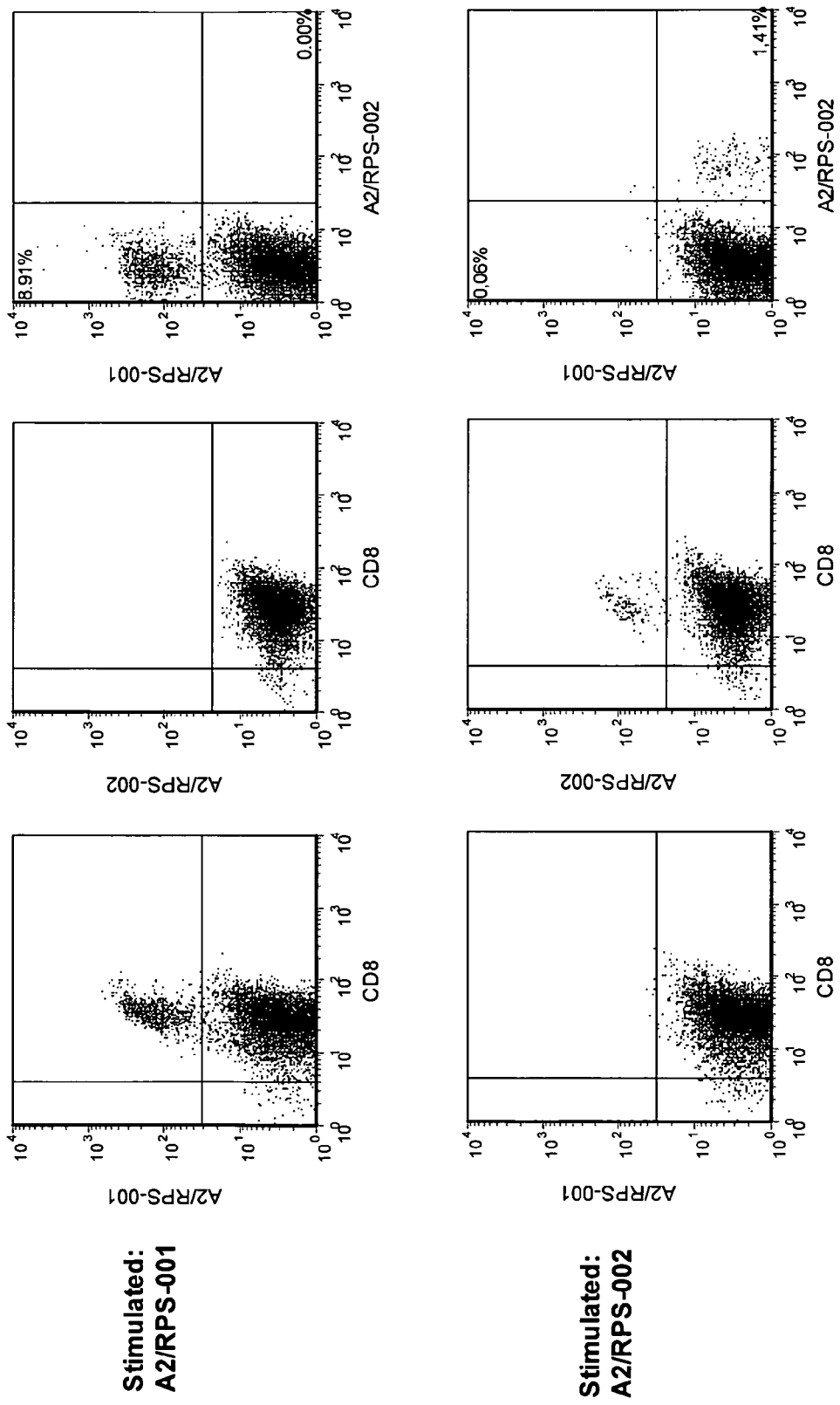
FIG. 12 shows the representative tetramer analysis of microsphere driven expansion of A2/RPS-001 and A2/RPS-002 specific CD8+ lymphocytes from peripheral blood. 1×106 CD8+ enriched PBMCs per well of the healthy HLA-A2+ donor HBC-065 were stimulated weekly in one well with microspheres coupled to anti-CD28 plus high density tumor antigen A*0201/RPS-001 (upper panel) or high density tumor antigen A*0201/RPS-002 (lower panel) as shown before [Walter, S, et al. Cutting Edge: Predetermined avidity of human CD8 T cells expanded on calibrated MHC/anti-CD28-coated microspheres. J. Immunol. 171(10):4974-8, 2003] with minor modifications. After three stimulations in vitro, cells of both wells were stained with antibody CD8 FITC plus tetramer A*0201/RPS-001 APC and A*0201/RPS-002 PE. Cells are gated on the lymphocyte population (left and middle panel) or on the CD8+ lymphocyte population (right panel). Numbers represent percentage of tetramer$^+$ within CD8+ lymphocytes. RPS-001=LLAARAIVAI (SEQ ID-No. 1); RPS-002=ALCNTDSPL (SEQ ID-No. 2)

In summary, the potential of peptides ILR1 and -2 from OFA-ILRP to evoke cellular immune responses against cancer cells, specifically from leukemias and lymphomas, becomes clearly visible. The T cells specific for these peptides display effector functions (secretion of IFN-γ gamma). Table 6: Summary of tetramer analysis of microsphere driven expansions of A2/RPS-001 and A2/RPS-002 specific CD8+ lymphocytes from peripheral blood. 1×10$^6$ CD8+ enriched PBMCs per well were stimulated as in FIG. 12 with microspheres coupled to anti-CD28 plus high density tumor antigen A*0201/RPS-001 or high density tumor antigen A*0201/RPS-002. Indicated are number of evaluable HLA-A2+ donors, number of evaluable donors with at least one clearly positive response, number of evaluable stimulations among all evaluable donors and number of evaluable stimulations with clearly positive responses. RPS001=LLAARAIVAI (SEQ ID-NO: 1); RPS-002=ALCNTDSPL (SEQ ID-NO: 2)

TABLE 6

| Antigen | Parameter | Value |
|---|---|---|
| A2/RPS-001 | Evaluable donors | 5 |
| A2/RPS-001 | Evaluable donors with clearly positive T-cell responses | 5 |
| A2/RPS-001 | Evaluable stimulations among all evaluable donors | 53 |
| A2/RPS-001 | Evaluable stimulations with clearly positive T-cell responses | 29 |
| A2/RPS-002 | Evaluable donors | 5 |
| A2/RPS-002 | Evaluable donors with clearly positive T-cell responses | 1 |
| A2/RPS-002 | Evaluable stimulations among all evaluable donors | 54 |
| A2/RPS-002 | Evaluable stimulations with clearly positive T-cell responses | 1 |

Further Experiments Regarding ILR1 (LLAARAIVAI)

T cells recognizing the ILR1-peptide were tested on K562 [human pro-erythroblastic leukemia cell-line, also known as chronic myelogenous leukemia (CML) cell line, which, due to extremely low levels of HLA, functions as a control for excluding NK cells as effector cells], IND (human B lymphoblastoid cell line), Karpas-422 (human B cell lymphoma), Balm-3 (human non-Burkitt B-lymphoma cell line), U266 (human multiple myeloma), REH (Human B cell precursor leukemia), MEC-1 (human chronic B cell leukemia). The same T cells were used to test autologous and allogeneic PBMC from healthy donors as controls. All cell lines except MEC-1, which does not express the HLA-A*02 allele, and K562, which is deficient for HLA class I gene expression in general, were recognized by the ILR1 specific T cells (see FIG. 1). Both allogeneic and autologous cells from healthy donors were not recognized, indicating that 1. ILR1 is significantly expressed on the peptide level only in tumor cells, but not in blood mononuclear cells from HLA-matched healthy donors.
2. The response is not directed against allogeneic major or minor histocompatibility complex antigens.
3. ILR1 peptide is recognized in an HLA-restricted fashion.
4. The restriction is allele-specific (specific for A*02).

Target: AML

Figure 4:
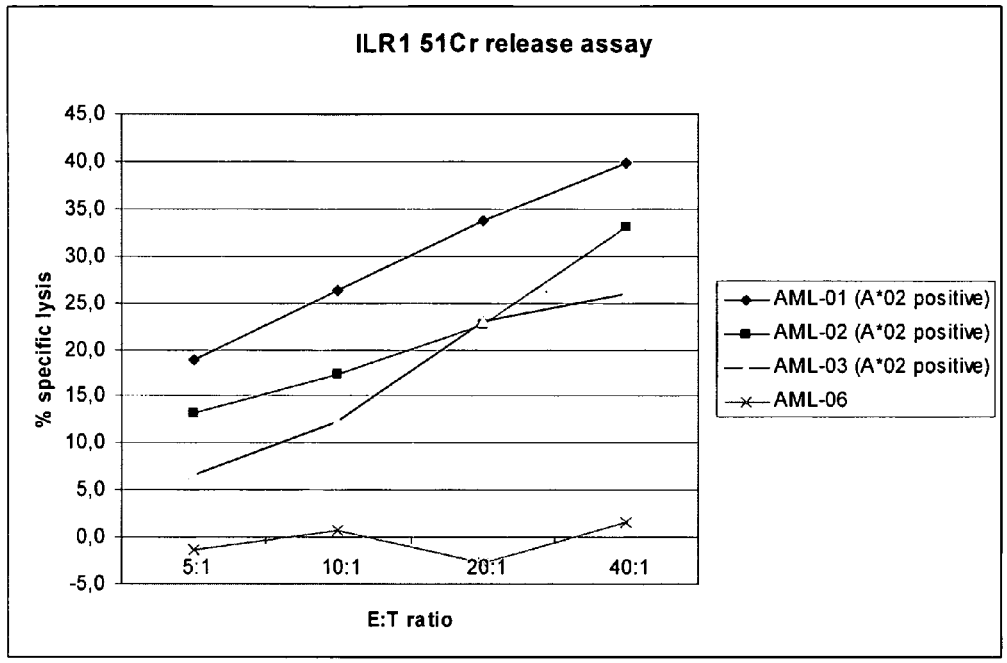
FIG. 4 shows that CTL specific for HLA-A*02/ILR1 kill tumor cells from AML patients; (A) 1$^{st}$ experiment; (B) 2nd experiment.
Figure 4:
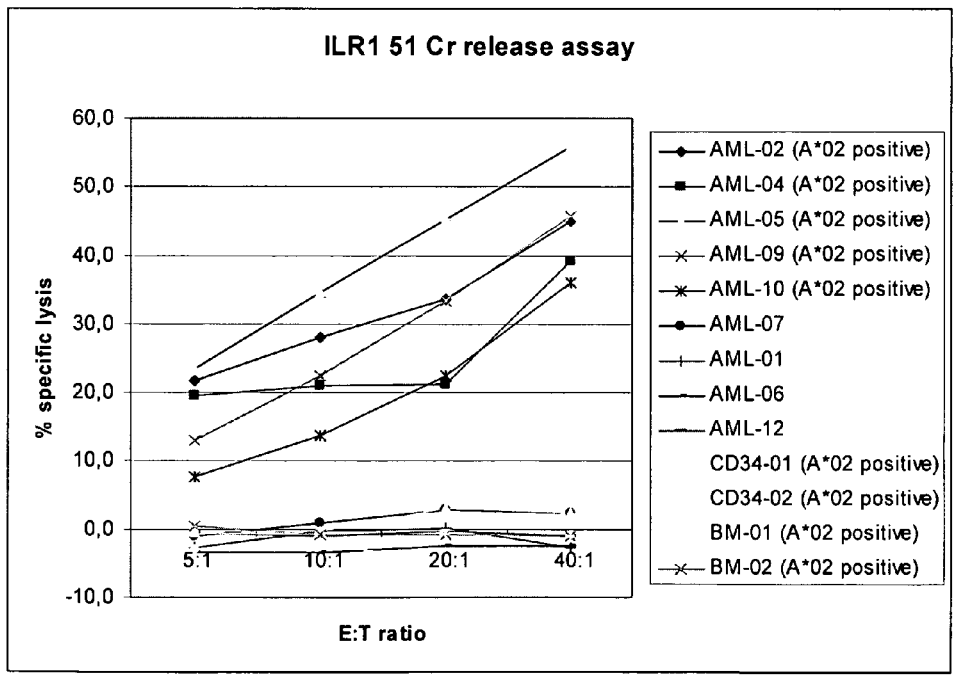
Figure 5A:
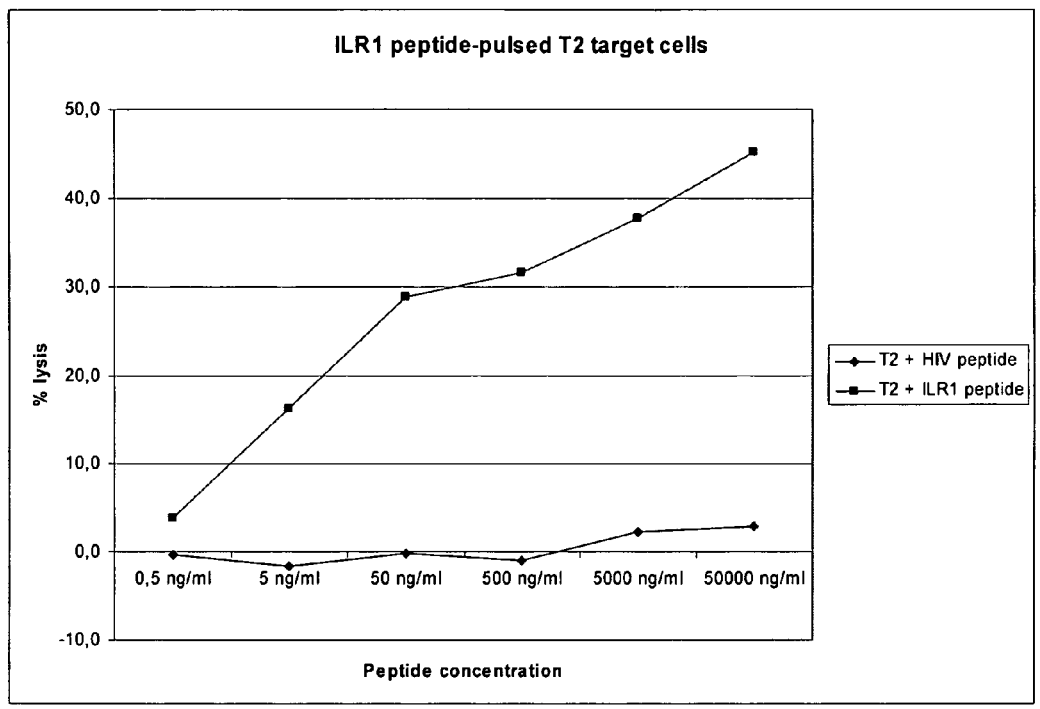
FIG. 5A shows the dose dependency of lysis of peptide-pulsed T2 target cells by ILR1-specific CTL.

T cells specific for HLA-A*02-restricted ILR1 were tested on tumor cells from AML patients (4 patients; samples AML-01, -02, -03, -06) (FIG. 4A). Cells from A*02-positive patients (3/4) were recognized with maximum lysis at an E:T ratio of 40:1 ranging between 25,9% and 39,8%. AML cells from A*02-negative patient AML-06 were not recognized.

T cells specific for HLA-A*02-restricted ILR1 were tested on tumor cells from AML patients for a second time to confirm the results obtained in the 1$^{st}$ experiment (9 patients; samples AML-01, -02, -04, -05, -06, -07, -09, -10, -12). Cells from A*02-positive patients (5/9; AML-02, -04, -05, -09, -10)) were recognized in all cases. Cells from A*02-negative patients (4/9; AML-01, -06, -07, -12) were not recognized (4/4) (FIG. 4B).

FIG. 4B also shows data on CD34-positive bone-marrow-derived progenitor cells from A*02-positive donors (CD34-01, -02), which were not recognized by activated ILR1-specific T cells, which had been re-stimulated with ILR1 in the presence of IL-2 in vitro for 7 days. Also, bone marrow cells (BM-01, -02) from A*02-positive donors were not recognized by these T cell clones.

Figure 2:
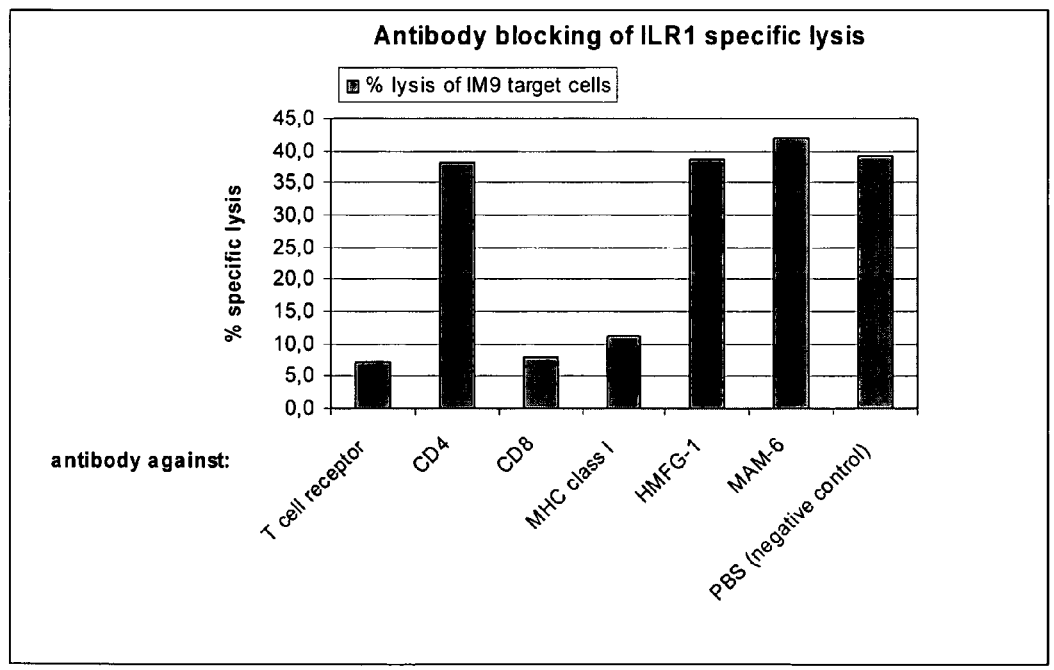
FIG. 2 shows the blocking of target cell lysis by antibodies recognizing CD8, MHC class I or TCR for ILR1.

FIG. 2 shows antibody blocking experiments to further characterize the specificity of the T cell response. Prior to 51Cr-release experiments at a constant E:T ratio of 40:1, blocking mAbs were incubated with the human B lymphoblastoid cell line IM-9 at mAb concentrations as indicated by the manufacturer. The blocking experiments indicate that the recognition of ILR1 is mediated by 1. Cells bearing T-cell receptors (TCR),
2. recognizing their target in the context of MHC class I (HLA class I), and 3. by a mechanism of interaction depending on the co-receptor CD8, but not CD4.

Control mAbs specific for irrelevant, mucin-like cell surface proteins MAM-6 (synonyms: CA 15-3, DF3) and HMFG-1 did not have an effect on the recognition of IM-9 cells by the effector T cells. PBS was used as a negative control in these blocking experiments.

In summary, these two sets of experiments confirm that
1. ILR1 is a tumor-associated antigen in 100% (8/8) of A*02-positive (8/13) AML patients tested.
2. ILR1 is restricted by HLA-A*02.
3. The ILR1-specific T cells recognize naturally processed ILR2 on tumor cells, while at the same time the ILR1 peptide seems to be absent on bone marrow and CD34 positive progenitor cells.
4. The interaction between targets and effector cells can be specifically inhibited with mAbs against MHC class I, TCR or CD8.

Target: CLL

Figure 3:
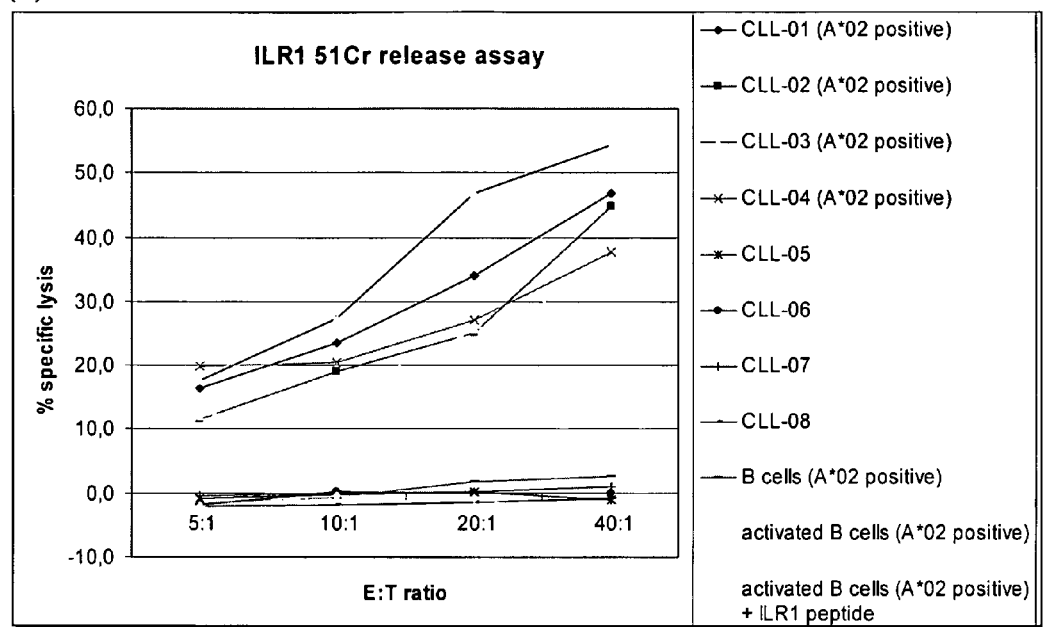
FIG. 3 shows that CTL specific for HLA-A*02/ILR1 kill tumor cells from CLL patients; (A) 1$^{st}$ experiment; (B) 2nd experiment.
Figure 3:
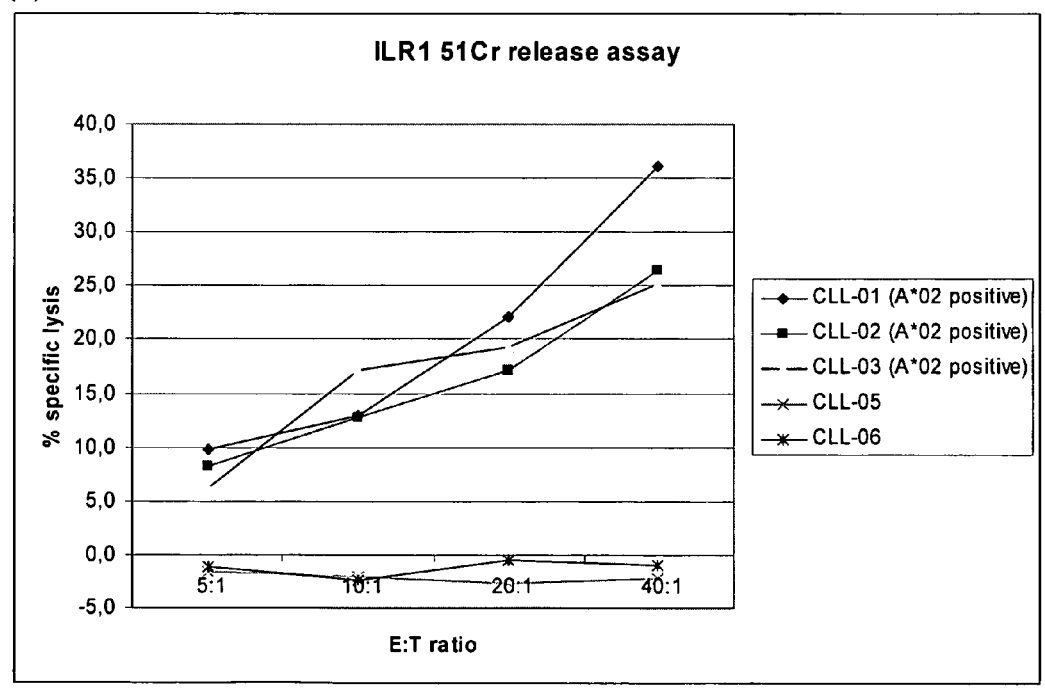

T cells specific for HLA-A*02-restricted ILR1 were tested on tumor cells from CLL patients (5 patients; samples CLL-01, -02, -03, -05, -06). Cells from A*02-positive patients (3/5) were-recognized-in-all cases (3/3). Cells from A*02-negative patients-were recognized in any case (0/2) (FIG. 3B). The experiment was repeated (FIG. 3A) with 8 more CLL patients, of whom 4/8 were A*02-positive. As CLL cells from 4/4 A*02-positive patients were recognized, while 0/4 A*02-negative target cells were recognized, these additional experiments confirmed the aforementioned results. In summary:
1. ILR1 is a tumor-associated antigen in 100% (7/7) of A*02-positive CLL patients tested.
2. ILR1 is restricted by HLA-A*02.

Target: T2

T2 cells are deficient for expression of TAP, the "Transporter associated with Antigen Processing," which is responsible for shuttling short peptides from the cytoplasm to the endoplasmatic reticulum (ER), where peptides are loaded onto empty MHC class I molecules. In consequence, MHC class I molecules of T2 cells remain empty, if no peptides are added (external loading). Thus, T2 cells expressing empty HLA-A*02 molecules on the cell surface are optimal targets for establishing titration curves for peptide-specific killing by HLA-A*02-restricted T cells.

In this experiment (FIG. 5A), T cells specific for ILR1 were tested on T2 cells pulsed with either a well-described T cell epitope from HIV, or with the ILR1 peptide LLAARAIVAI (SEQ ID NO:1). Results: the T cells recognized only T2 cells pulsed with the ILR1 peptide. T2 cells pulsed with the HIV peptide were not recognized. ILR1 peptide-pulsed T2 targets were lysed in a dose-dependent fashion. Lysis did not reach saturation in the range of concentrations tested.

Target: T2+ILR1

Figure 5B:
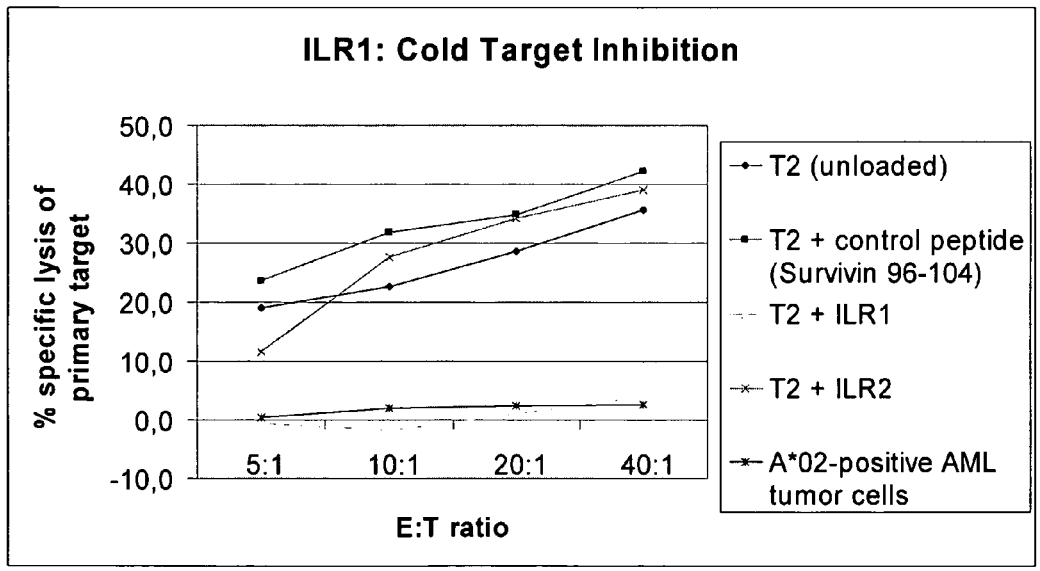
FIG. 5B shows the inhibition of ILR1-specific CTL by cold targets (Cold Target Inhibition Assay).
Figure 6:
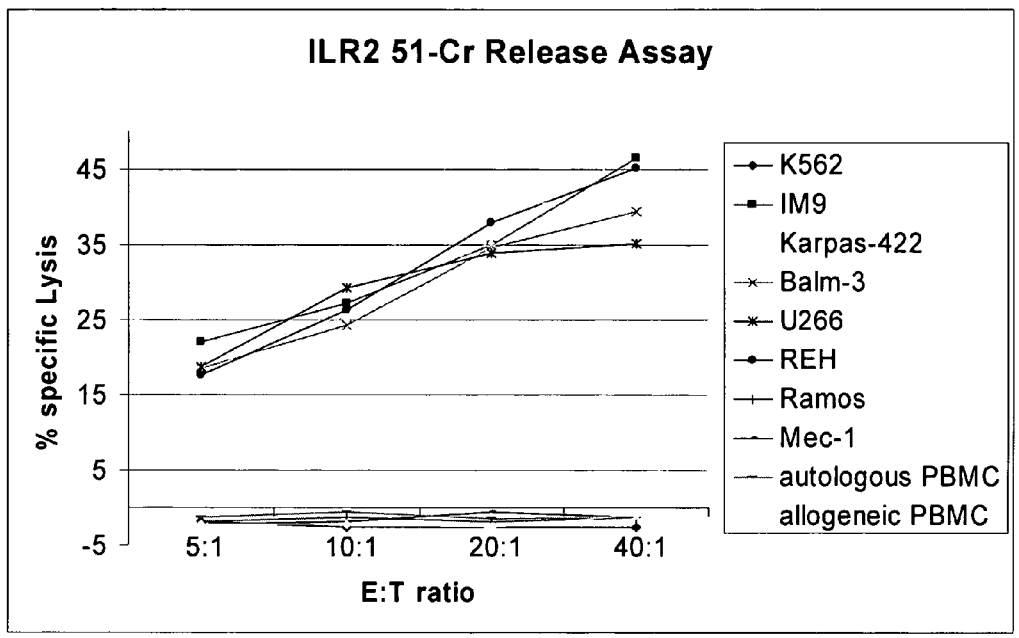
FIG. 6 shows the recognition of various cell lines by CTL specific for ILR2.

A cold target inhibition assay was performed. To examine whether ILR1-specific T cells lyse ILR1 peptide-pulsed T2 cells specifically and in the context of HLA-A*02, cold target inhibition assays were performed as follows: $^{51}$Cr-labelled T2 cells were loaded with peptide in a concentration of 10 microgram peptide/$10^6$ T2 cells/ml. A total of $2\times10^5$ unlabelled, T2 cells, which had equally been loaded with the same or a control peptide, were then added in a volume of 50 microliter AIMV to $10^4$ peptide-pulsed, $^{51}$Cr-labelled T2 cells. Effector T cells specific for ILR1 were added and a $^{51}$Cr-release assay was performed as described above. The analysis demonstrates that neither peptides irrelevant for ILR1-specific CTL (Survivin and ILR2), nor unloaded T2 cells, which display empty HLA-A*02 molecules on their cell surfaces, compete for lysis of targets loaded with ILR1 peptide by ILR1-specific CTL. To the contrary, once targets pulsed with synthetic ILR1 peptide, or AML tumor cells naturally displaying ILR1 in the context of HLA-A*02, are used as secondary (cold) targets, then these compete with the primary target cells (hot, ILR1-peptide-pulsed T2) for lysis by the ILR1-specific CTL (FIG. 5B).

Further Experiments Regarding ILR2 (ALCNTDSPL)

T cells recognizing the ILR2-peptide (FIG. 6) were tested on K562 [human proerythroblastic leukemia cell-line, also known as chronic myelogenous leukemia (CML) cell line, which, due to extremely low levels of HLA, functions as a control for excluding NK cells as effector cells], IM9 (human B lymphoblastoid cell line), Karpas-422 (human B cell lymphoma), Balm-3 (human non-Burkitt B-lymphoma cell line), U266 (human multiple myeloma), REH (Human B cell precursor leukemia), Ramos (synonym: RA 1; a human Burkittt's lymphoma B lymphoblast), MEC-1 (human chronic B cell leukemia). The same T cells were used to test autologous and allogeneic PBMC from healthy donors as controls.

All cell lines except Ramos and MEC-1, which do not express the HLA-A*02 allele, and K562, which is deficient for HLA class I gene expression in general, were recognized by the ILR2 specific T cells. Both allogeneic and autologous cells from healthy donors were not recognized, indicating that:
1. ILR2 is significantly expressed on the peptide level only in tumor cells, but not in blood mononuclear cells from HLA-matched healthy donors.
2. The response is not directed against allogeneic major or minor histocompatibility complex antigens.
3. ILR2 peptide is recognized in an HLA-restricted fashion.
4. The restriction is allele-specific (specific for A*02).

Target: AML

Figure 8:
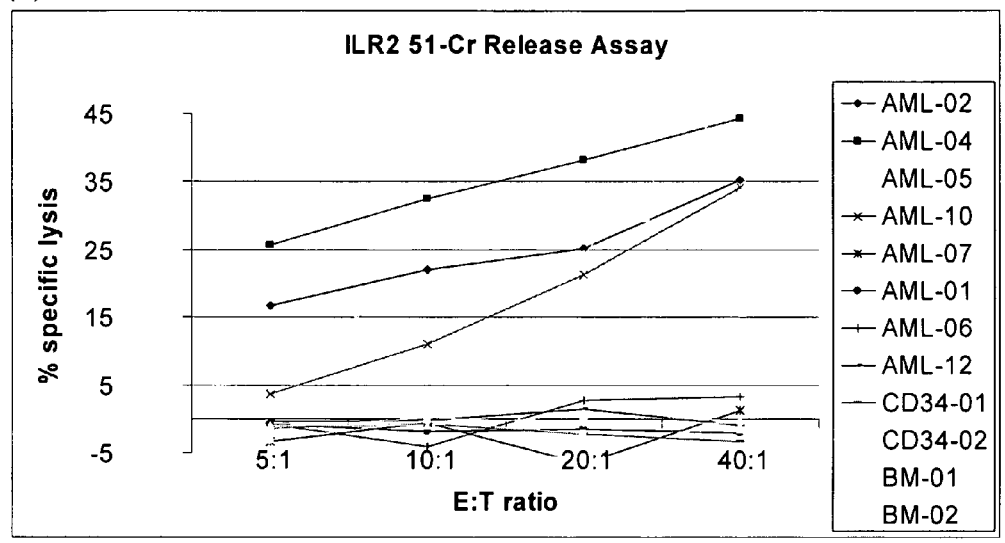
FIG. 8 shows that CTL specific for HLA-A*02/ILR2 kill tumor cells from AML patients. (A) 1$^{st}$ experiment; (B) 2nd experiment.
Figure 8:
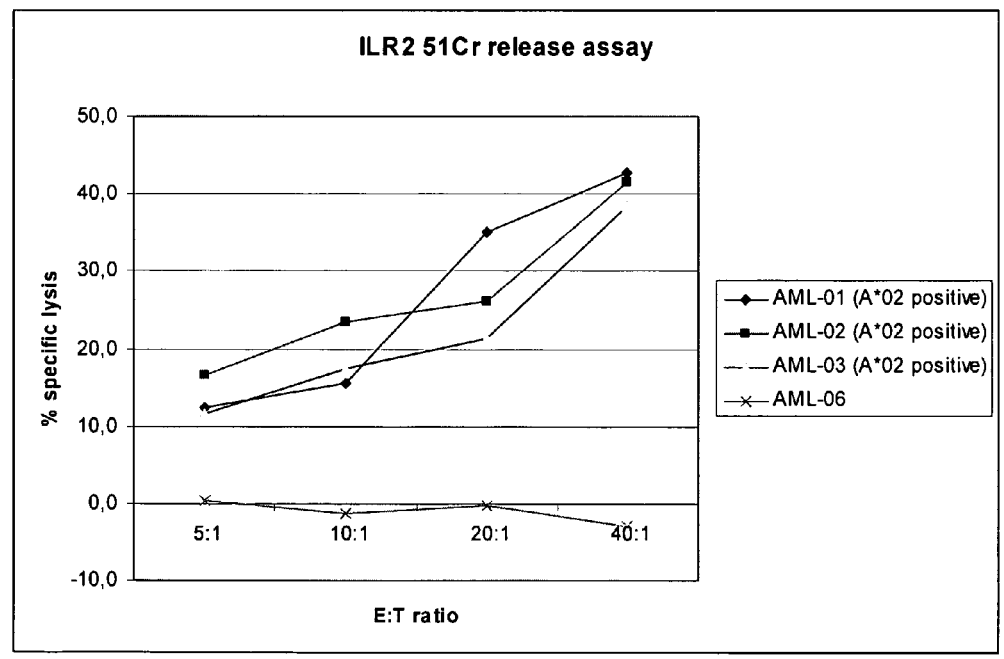

T cells specific for HLA-A*02-restricted ILR2 were tested on tumor cells from AML patients (8 patients; samples AML-01, -02, -04, -05, -06, -07, -10, -12). Cells from A*02-positive patients (4/8; AML-02, -04, -05, -10) were recognized in all cases (4/4). Cells from A*02-negative patients (4/8; AML-01, -06, -07, -12) were not recognized (4/4) (FIG. 8A). The experiment was conducted a $2^{nd}$ time with samples from patients who had not been tested before. In this $2^{nd}$ experiment, T cells specific for HLA-A*02-restricted ILR2 were tested again on tumor cells from AML patients (4 patients; samples AML-01, -02, -03, -06). Cells from A*02-positive patients (3/4) were recognized in all cases. Cells from A*02-negative patients were not recognized (0/1) (FIG. 8B).

FIG. 8A shows data on CD34-positive bone-marrow-derived progenitor cells from A*02-positive donors (CD34-01, -02), which were not recognized by activated ILR2-specific T cells, which had been re-stimulated with ILR2 in the presence of IL-2 in vitro for 7 days. Also, bone marrow cells (BM-01, -02) from A*02-positive donors were not recognized by these T cell clones.

Figure 7:
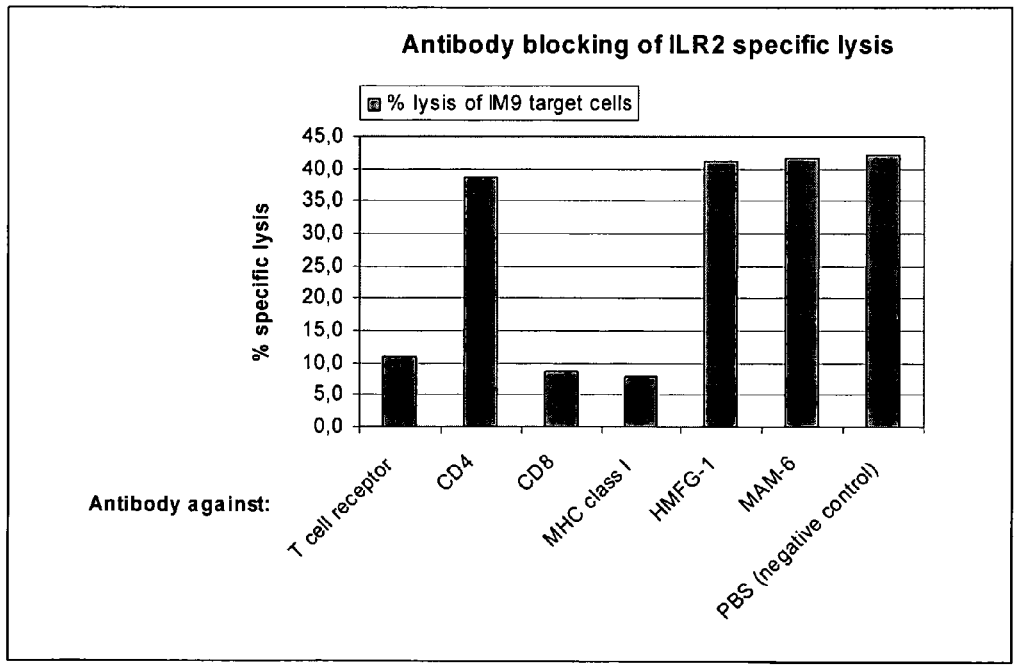
FIG. 7 shows the blocking of target cell lysis by antibodies recognizing CD8, MHC class I or TCR for ILR2.

FIG. 7 shows antibody blocking experiments to further characterize the specificity of the T cell response. Prior to 51Cr-release experiments at a constant E:T ratio of 40:1, blocking mAbs were incubated with the human B lymphoblastoid cell line IM-9 at mAb concentrations as indicated by the manufacturer. The blocking experiments indicate that the recognition of ILR2 is mediated by Cells bearing T-cell receptors (TCR), recognizing their target in the context of MHC class I (HLA class I), by a mechanism of interaction depending on the coreceptor CD8, but not CD4.

Control mAbs specific for irrelevant, mucin-like cell surface proteins MAM-6 (synonyms: CA 15-3, DF3) and HMFG-1 did not have an effect on the recognition of IM-9 cells by the effector T cells. PBS was used as a negative control in these blocking experiments. In summary, these two sets of experiments confirm that:

1. ILR2 is a tumor-associated antigen in 100% (7/7) of A*02-positive AML patients tested.
2. ILR2 is restricted by HLA-A*02.
3. The ILR2-specific T cells recognize naturally processed ILR2 on tumor cells, while at the same time the ILR2 peptide seems to be absent on bone marrow and CD34 positive progenitor cells.
4. The interaction between targets and effector cells can be specifically inhibited with mAbs against MHC class I, TCR or CD8.

Target: CLL

Figure 9:
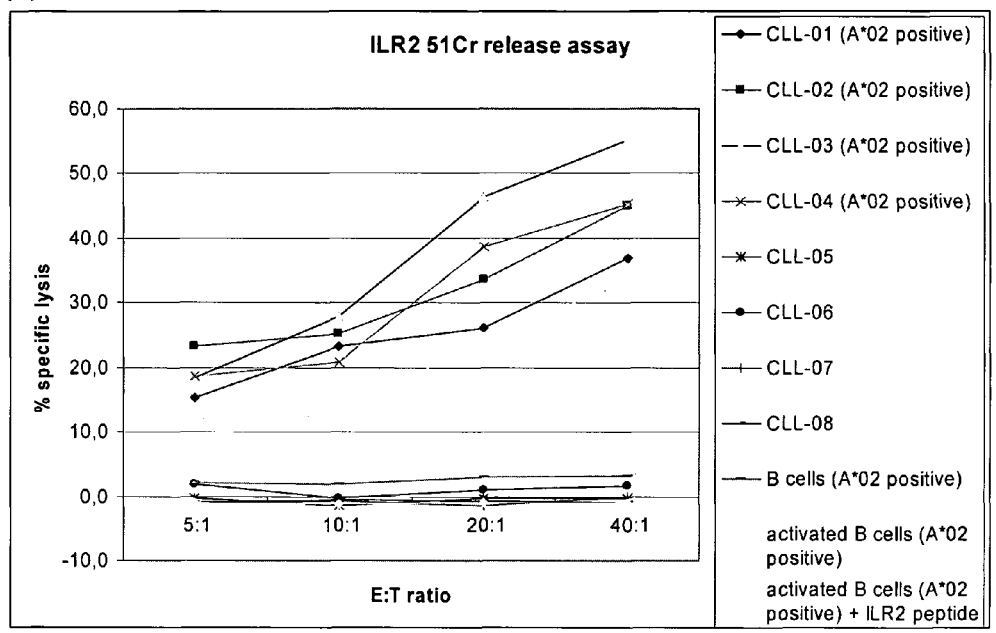
FIG. 9 shows that CTL specific for HLA-A*02/ILR2 kill tumor cells from CLL patients. (A) 1$^{st}$ experiment; (B) 2nd experiment.
Figure 9:
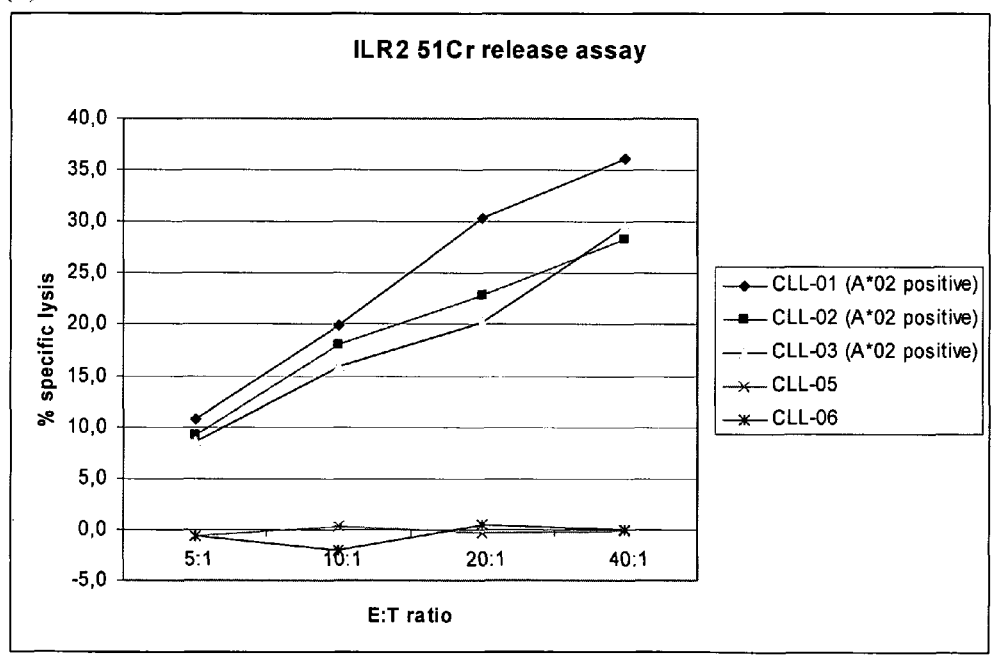

T cells specific for HLA-A*02-restricted ILR2 were tested on tumor cells from CLL patients (8 patients; samples CLL-01, -02, -03, -04, -05, -06, -07, -08). Cells from A*02-positive patients (4/8) were recognized in all cases (4/4). Cells from A*02-negative patients were not recognized in any case (0/4) (FIG. 9A). The experiment was repeated (FIG. 9B) with 5 more CLL patients, of whom 3/5 were A*02-positive. As CLL cells from 3/3 A*02-positive patients were recognized, while 0/2 A*02-negative target cells were recognized, these additional experiments confirmed the aforementioned results. Conclusion and summary:

1. ILR2 is a tumor associated antigen in 100% (7/7) of A*02-positive CLL patients tested.
2. ILR2 is restricted by HLA-A*02.

Target: T2

Figure 10A:
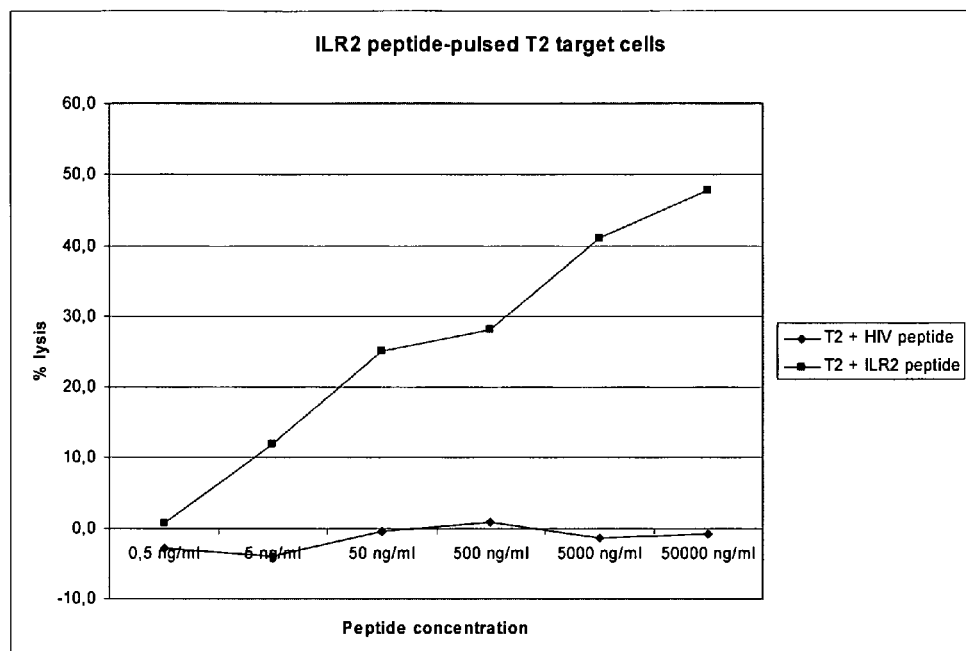
FIG. 10A shows the dose dependency of lysis of peptide-pulsed T2 target cells by ILR2-specific CTL.

T2 cells are deficient for expression of TAP, the "Transporter associated with Antigen Processing," which is responsible for shuttling short peptides from the cytoplasm to the Endoplasmatic Reticulum (ER), where peptides are loaded onto empty MHC class I molecules. In consequence, MHC class I molecules of T2 cells remain empty, if no peptides are added (external loading). Thus, T2 cells expressing empty HLA-A*02 molecules on the cell surface are optimal targets for establishing titration curves for peptide-specific killing by HLA-A*02-restricted T cells. In this experiment, T cells specific for ILR2 were tested on T2 cells pulsed with either a well-described T cell epitope from HIV, or with the ILR2 peptide ALCNTDSPL. Results: the T cells recognized only T2 cells pulsed with the ILR2 peptide. T2 cells pulsed with the HIV peptide were not recognized. ILR2 peptide-pulsed T2 targets were lysed in a dose-dependent fashion. Lysis did not reach saturation in the range of concentrations tested (FIG. 10A).

Target: T2+ILR2

Figure 10B:
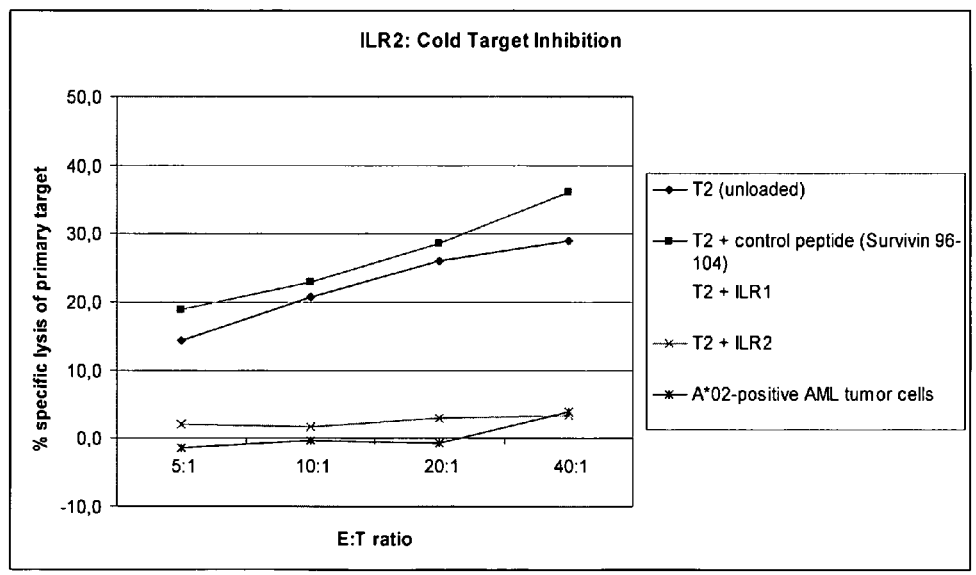
FIG. 10B shows the inhibition of ILR2-specific CTL by cold targets (Cold Target Inhibition Assay).

A cold target inhibition assay was performed as described under "T2+ILR1" above. The results from this experiment confirm that neither peptides irrelevant for ILR2-specific CTL (Survivin and ILR1), nor unloaded T2 cells, which display empty HLA-A*02 molecules on their cell surfaces, compete for lysis of targets loaded with ILR2 peptide by ILR2-specific CTL. To the contrary, once targets pulsed with synthetic ILR2 peptide, or AML tumor cells naturally displaying ILR2 in the context of HLA-A*02, are used as secondary (cold) targets, then these compete with the primary target cells (hot, ILR2-peptide-pulsed T2) for lysis by the ILR2-specific CTL (FIG. 10B).

In summary, both inventive peptides from ILR are candidates for developing peptide based therapeutic vaccines for cancer patients in general.

The invention claimed is:

1. A tumor associated peptide consisting of SEQ ID NO: 1 wherein the peptide has the ability to bind to the human major histocompatibility complex (MHC) class-I HLA-A*0201 molecule.

2. A method of producing the tumor associated peptide of claim 1, the method comprising culturing a host cell comprising an expression vector capable of expressing a nucleic acid encoding the tumor associated peptide in a culture medium under conditions wherein the nucleic acid is expressed, and isolating the peptide from the host cell and/or culture medium thereof.

3. A pharmaceutical composition comprising the tumor associated peptide of claim 1 and a pharmaceutically acceptable carrier.

4. The pharmaceutical composition according to claim 3 further comprising
a tumor associated peptide consisting of SEQ ID NO: 2, and optionally an N-terminal extension 1 to 10 amino acids in length and optionally a C-terminal extension 1 to 10 amino acids in length.

5. A cancer vaccine comprising the tumor associated peptide of claim 1.

6. An in vitro method for producing activated cytotoxic T lymphocytes (CTL), the method comprising contacting in vitro CTL with antigen loaded human class I MHC molecules expressed on the surface of a suitable antigen-presenting cell for a period of time sufficient to activate, in an antigen specific manner, said CTL wherein the antigen is the peptide of claim 1 and wherein the class I MHC molecule is HLA-A*0201.

7. The method according to claim 6, wherein the antigen is loaded onto class I MHC molecules expressed on the surface of a suitable antigen-presenting cell by contacting a sufficient amount of the antigen with an antigen-presenting cell.

8. The method according to claim 6, wherein the antigen-presenting cell comprises an expression vector capable of expressing a nucleic acid encoding the peptide of claim 1.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Homo sapiens

<400> SEQUENCE: 1

Leu Leu Ala Ala Arg Ala Ile Val Ala Ile
1               5                   10

<210> SEQ ID NO 2
<211> LENGTH: 9
<212> TYPE: PRT
<213> ORGANISM: Homo sapiens

<400> SEQUENCE: 2

Ala Leu Cys Asn Thr Asp Ser Pro Leu
1               5

<210> SEQ ID NO 3
<211> LENGTH: 9
<212> TYPE: PRT
<213> ORGANISM: Homo sapiens

<400> SEQUENCE: 3

Gly Ile Leu Gly Phe Val Phe Thr Leu
1               5

<210> SEQ ID NO 4

```
<211> LENGTH: 9
<212> TYPE: PRT
<213> ORGANISM: Homo sapiens

<400> SEQUENCE: 4

Ile Leu Lys Glu Pro Val His Gly Val
1               5

<210> SEQ ID NO 5
<211> LENGTH: 9
<212> TYPE: PRT
<213> ORGANISM: Homo sapiens

<400> SEQUENCE: 5

Leu Tyr Leu Lys Asn Tyr Arg Ile Ala
1               5

<210> SEQ ID NO 6
<211> LENGTH: 9
<212> TYPE: PRT
<213> ORGANISM: Homo sapiens

<400> SEQUENCE: 6

Leu Ala Ala Arg Ala Ile Val Ala Ile
1               5

<210> SEQ ID NO 7
<211> LENGTH: 9
<212> TYPE: PRT
<213> ORGANISM: Homo sapiens

<400> SEQUENCE: 7

Leu Leu Leu Ala Ala Arg Ala Ile Val
1               5

<210> SEQ ID NO 8
<211> LENGTH: 9
<212> TYPE: PRT
<213> ORGANISM: Homo sapiens

<400> SEQUENCE: 8

Val Leu Gln Met Lys Glu Glu Asp Val
1               5

<210> SEQ ID NO 9
<211> LENGTH: 9
<212> TYPE: PRT
<213> ORGANISM: Homo sapiens

<400> SEQUENCE: 9

Asn Leu Lys Arg Thr Trp Glu Lys Leu
1               5

<210> SEQ ID NO 10
<211> LENGTH: 9
<212> TYPE: PRT
<213> ORGANISM: Homo sapiens

<400> SEQUENCE: 10

Val Ala Ile Glu Asn Pro Ala Asp Val
1               5

<210> SEQ ID NO 11
<211> LENGTH: 9
<212> TYPE: PRT
<213> ORGANISM: Homo sapiens
```

```
<400> SEQUENCE: 11

Tyr Val Asn Leu Pro Thr Ile Ala Leu
1               5

<210> SEQ ID NO 12
<211> LENGTH: 9
<212> TYPE: PRT
<213> ORGANISM: Homo sapiens

<400> SEQUENCE: 12

Met Leu Ala Arg Glu Val Leu Arg Met
1               5

<210> SEQ ID NO 13
<211> LENGTH: 9
<212> TYPE: PRT
<213> ORGANISM: Homo sapiens

<400> SEQUENCE: 13

Ser Glu Gly Val Gln Val Pro Ser Val
1               5

<210> SEQ ID NO 14
<211> LENGTH: 9
<212> TYPE: PRT
<213> ORGANISM: Homo sapiens

<400> SEQUENCE: 14

Phe Leu Ala Ala Gly Thr His Leu Gly
1               5

<210> SEQ ID NO 15
<211> LENGTH: 10
<212> TYPE: PRT
<213> ORGANISM: Homo sapiens

<400> SEQUENCE: 15

Lys Leu Leu Leu Ala Ala Arg Ala Ile Val
1               5                   10

<210> SEQ ID NO 16
<211> LENGTH: 10
<212> TYPE: PRT
<213> ORGANISM: Homo sapiens

<400> SEQUENCE: 16

Ala Ile Glu Asn Pro Ala Asp Val Ser Val
1               5                   10

<210> SEQ ID NO 17
<211> LENGTH: 10
<212> TYPE: PRT
<213> ORGANISM: Homo sapiens

<400> SEQUENCE: 17

Leu Met Trp Trp Met Leu Ala Arg Glu Val
1               5                   10
```